US012747439B2

(12) United States Patent
Raymond et al.

(10) Patent No.: US 12,747,439 B2
(45) Date of Patent: Sep. 29, 2026

(54) NUTRITIONAL COMPOSITION COMPRISING MIR-3126

(71) Applicant: SOCIETE DES PRODUITS NESTLE S.A., Vevey (CH)

(72) Inventors: Frederic Raymond, Chatel-St-Denis (CH); Mohamed Nabil Bosco, Epalinges (CH); Lorane Texari, Morges (CH); Solenn Pruvost, Cessy (FR); Gregory Lefebvre, Vullierens (CH)

(73) Assignee: Societe des Produits Nestle S.A., Vevey (CH)

( * ) Notice: Subject to any disclaimer, the term of this patent is extended or adjusted under 35 U.S.C. 154(b) by 698 days.

(21) Appl. No.: 18/015,105

(22) PCT Filed: Jul. 7, 2021

(86) PCT No.: PCT/EP2021/068775

§ 371 (c)(1),
(2) Date: Jan. 9, 2023

(87) PCT Pub. No.: WO2022/008572

PCT Pub. Date: Jan. 13, 2022

(65) Prior Publication Data

US 2023/0250427 A1 Aug. 10, 2023

(30) Foreign Application Priority Data

Jul. 10, 2020 (EP) .................................... 20185307

(51) Int. Cl.

| | |
|---|---|
| ***C12N 15/113*** | (2010.01) |
| ***A23L 33/00*** | (2016.01) |
| ***A23L 33/13*** | (2016.01) |

(52) U.S. Cl.

CPC ............ *C12N 15/113* (2013.01); *A23L 33/13* (2016.08); *A23L 33/40* (2016.08); *C12N 2310/141* (2013.01); *C12N 2320/30* (2013.01)

(58) Field of Classification Search

CPC .... A23L 33/00; A23L 33/40; C12N 2310/141
See application file for complete search history.

(56) References Cited

U.S. PATENT DOCUMENTS

2015/0366897 A1 12/2015 Stevanato et al.
2016/0017321 A1* 1/2016 Zhang .................. C12N 15/111 435/320.1

FOREIGN PATENT DOCUMENTS

| | | | |
|---|---|---|---|
| CN | 103209601 | A | 7/2013 |
| CN | 103924002 | A | 7/2014 |
| CN | 108113995 | A | 6/2018 |
| EP | 2896294 | | 7/2015 |
| RU | 2017101354 | A | 7/2018 |

OTHER PUBLICATIONS

Ahern, Grace J., et al. “Advances in Infant Formula Science.” Annual Review of Food Science and Technology, vol. 10, No. 1, Mar. 25, 2019, pp. 75-102, https://doi.org/10.1146/annurev-food-081318-104308. (Year: 2019).*

Allen, Jonathan. “New Yorkers Sample Cheese Made from Human Breast Milk.” Reuters, May 2, 2011, www.reuters.com/article/lifestyle/new-yorkers-sample-cheese-made-from-human-breast-milk-idUSTRE7413X0/. (Year: 2011).*

Raymond, Frederic, et al. “Longitudinal Human Milk MiRNA Composition over the First 3 Mo of Lactation in a Cohort of Healthy Mothers Delivering Term Infants.” The Journal of Nutrition, vol. 152, No. 1, Sep. 11, 2021, pp. 94-106, www.sciencedirect.com/science/article/pii/S0022316622005028?via%3Dihub (Year: 2021).*

Raymond, Frederic, et al. “Longitudinal Human Milk MiRNA Composition over the First 3 Mo of Lactation in a Cohort of Healthy Mothers Delivering Term Infants.” Supplemental Material. The Journal of Nutrition, vol. 152, No. 1, Sep. 11, 2021, pp. 94-106. (Year: 2021).*

The Purefood Co. “What Is Food Fortification? How Does It Work?” Thepurefoodco.com, Jul. 19, 2017, thepurefoodco.com/aus/enhancing-our-meals-with-food-fortification/. Accessed Oct. 1, 2025. (Year: 2017).*

Zhang, Lin, et al. “Dietary MicroRNA—a Novel Functional Component of Food.” Advances in Nutrition, vol. 10, No. 4, Jul. 1, 2019, pp. 711-721, https://doi.org/10.1093/advances/nmy127. Accessed Apr. 27, 2023. (Year: 2019).*

Kosaka et al. “microRNA as a new immune-regulatory agent in breast milk” Silence, 2010, vol. 1, No. 7, 8 pages.

Zhou et al. “Immune-related MicroRNAs are Abundant in Breast Milk Exosomes” International Journal of Biological Sciences, 2012, vol. 8, No. 1, pp. 118-123.

Li et al. “Estrogen receptor β upregulated by lncRNA-H19 to promote cancer stem-like properties in papillary thyroid carcinoma” Cell Death & Disease, 2018, vol. 9, No. 1120, 15 pages.

Lu et al.; Maternal aryl hydrocarbon receptor activation protects newborns against necrotizing enterocolitis; Nature Communications | (2021)12:1042 | https://doi.org/10.1038/s41467-021-21356-4 | www.nature.com/naturecommunications; pp. 1-14.

Mezu-Ndubuisi et al; The role of integrins in inflammation and angiogenesis: Pediatric Research; Revised: Aug. 18, 2020 Accepted: Sep. 10, 2020 Published online: Oct. 7, 2020; (8 pages).

Sheng et al; Phosphatidylinositol 3-kinase mediates proliferative signatls in intestinal ephithelial cells; Home/Archive/vol. 52, Issue 10; https://gut.bmj.com/content/52/10/1472 (5 pages).

(Continued)

*Primary Examiner* — Kimberly Chong
*Assistant Examiner* — Africa M McLeod
(74) *Attorney, Agent, or Firm* — K&L Gates LLP

(57) ABSTRACT

A nutritional composition comprising miR-3126. miR-3126 or said nutritional composition for use as a medicament. Use of miR-3126 to modulate gene expression of one or more gene selected from: Ninein, Unc-13 homolog D, Sulfatase 2, IL-32, OXER1, TMEM127, Butyrophilin, Integrin subunit alpha 2, Integrin beta 1, tubulin alpha 4A, tubulin beta 6, tubulin beta 2A and tubulin beta 2B. A method of producing said nutritional composition.

11 Claims, No Drawings

Specification includes a Sequence Listing.

(56) References Cited

OTHER PUBLICATIONS

Golan-Gerstl, et al. Characterization and biological function of milk-derived miRNAs; Molecular Nutrition and Food Research; (26 pages).
Korpal et al.; The miR-200 Family Inhibits Epithelial-Mesenchymal Transition and Cancer Cell Migratio by Direct Targeting of E-cadherin Transcriptional Repressors ZEB1 and ZEB2; From the Department of Molecular Biology, Princeton University. Princeton, New Jersey 0854;and in revised from, Apr. 14, 2008 Published, JBC Papers in Press, Apr. 14, 2008, DOI 10.1074/jbc.C80007420 (5 pages).
Zhang et al. "Serum microRNA Panel for Early Diagnosis of the Onset of Hepatocellular Carcinoma", Medicine, vol. 96, Issue No. 2, 2017, pp. 1-8.
Qin et al., "The Tumor Susceptibility Gene TMEM127 is Mutated in Renal Cell Carcinomas and Modulates Endolysosomal Function", Human Molecular Genetics, vol. 23, Issue No. 9, 2014, pp. 2428-2439.
Badri et al. "Optimization of Radiation Dosing Schedules for Proneural Glioblastoma" Journal of Mathematical Biology, vol. 72, 2016, pp. 1301-1336.
Jiang et al., "SULF2 Promotes Tumorigenesis and Inhibits Apoptosis of Cervical Cancer Cells Through the ERK/AKT Signaling Pathway", Brazilian Journal of Medical and Biological Research, vol. 53, Issue No. 2, 2020, pp. 1-11.
Qin et al. "Germline Mutations in TMEM127 Confer Susceptibility to Pheochromocytoma", Nature Genetics, vol. 42, Issue No. 3, 2010, pp. 1-19.
Baylot et al., "TCTP Has a Crucial Role in the Different Stages of Prostate Cancer Malignant 4 Progression 5", TCTP/tptl—Remodeling Signaling from Stem Cell to Disease, 2017, pp. 255-261.
Hanna et al., "The Potential for microRNA Therapeutics and Clinical Research", Frontiers in Genetics, vol. 10, 2019, pp. 1-6.
Muller et al., "Spliceosomal Peptide P140 for Immunotherapy of Systemic Lupus Erythematosus: Results of an Early Phase II Clinical Trial", Arthritis & Rheumatism, vol. 58, Issue No. 12, 2008, pp. 3873-3883.
Snow et al., "Ineffective Delivery of Diet-derived microRNAs to Recipient Animal Organisms" RNA Biology, vol. 10, Issue No. 7, 2013, pp. 1107-1116.

* cited by examiner

NUTRITIONAL COMPOSITION COMPRISING MIR-3126

CROSS REFERENCE TO RELATED APPLICATIONS

The present application is a National Stage of International Application No. PCT/EP2021/068775, filed on Jul. 7, 2021, which claims priority to European Patent Application No. 20185307.4, filed on Jul. 10, 2020, the entire contents of which are being incorporated herein by reference.

Sequence Listing

The instant application contains a Sequence Listing which has been submitted electronically in ASCII text file format and is hereby incorporated by reference in its entirety. Said ASCII text file copy, created on Mar. 30, 2026, is named 3712036-04441_SL.txt and is 13,447 bytes in size.

FIELD OF THE INVENTION

The present invention relates to nutritional compositions comprising miR-3126. The present invention also relates to uses of miR-3126 and said nutritional compositions and methods of producing said nutritional compositions.

BACKGROUND TO THE INVENTION

MicroRNAs (miRNAs) are small, non-coding RNAs around 17-25 nucleotides in length. They are regulatory RNA molecules that function to regulate the activity of specific mRNA targets and play important roles in a wide range of physiologic and pathologic processes. De-regulation of miRNA expression has been shown to have an impact on health and diseases (Wang et al. 2016, J. Cell Phys. 231:25-30).

Breast milk produced by mammals during lactation naturally contains miRNA. Milk miRNAs are found as free molecules but also packaged in microvesicles such as milk exosomes and fat globules. During lactation of a mother to infant, breast milk not only supplements nutrients to an infant, but also transfers miRNA between the mother and infant. This may promote healthy growth and development of the infant (Tome-Carneiro et al. 2018, Pharma. Res. 132:21-25).

While the beneficial effects of breast milk for the infant are known, not all infants have access to natural breast milk. Therefore, there is a need for nutritional compositions which mimic natural breast milk. In particular, there is a need to mimic the natural composition of breast milk at different stages of lactation as expression of these miRNA regulatory molecules correspond to the different growth and development needs of the infant over time after birth. In this regard, miRNA may be considered as an important component in breast milk during the different stages of lactation.

SUMMARY OF THE INVENTION

The present inventors have found that miR-3126 is present in natural breast milk. In particular, the present inventors have found that expression of miR-3126 in natural breast milk increases between two weeks and three months postpartum. Further, miR-3126 might be implicated in the health and development of infants.

In one aspect the present invention provides a nutritional composition comprising miR-3126. The nutritional composition may be an infant formula, a fortifier, or a supplement. Preferably, the nutritional composition is an infant formula.

The miR-3126 may be present in a concentration of 0.1-10000 pmol/L, 0.1-1000 pmol/L, 1-1000 pmol/L, 10-1000 pmol/L, or 100-1000 pmol/L. Preferably, the miR-3126 is present in a concentration of 10-1000 pmol/L. More preferably, the miR-3126 is present in a concentration of 100-1000 pmol/L.

The nutritional composition may comprise one or more additional microRNAs selected from the list consisting of: let-7b, let-7c, miR-19b, miR-22, miR-24, miR-25, miR-29a, miR-30a, miR-92a, miR-99a, miR-100, miR-197, miR-30d, miR-181a, miR-181b, miR-205, miR-210, miR-221, miR-125b, miR-125a, miR-149, miR-193a, miR-320a, miR-200a, miR-99b, miR-130b, miR-30e, miR-375, miR-378a, miR-151a, miR-425, miR-484, miR-146b, miR-574, miR-652, miR-320c, miR-3141, let-7d, miR-196a, miR-187, miR-516a, miR-92b, and miR-3184. Preferably, the nutritional composition comprises one or more additional microRNAs selected from the list consisting of: let-7d, miR-196a, miR-187, miR-516a, miR-92b, and miR-3184. More preferably, the nutritional composition comprises miR-3184 and/or miR-3141. The one or more additional microRNAs may be present in a concentration of 0.1-10000 pmol/L, 0.1-1000 pmol/L, 1-1000 pmol/L, 10-1000 pmol/L, or 100-1000 pmol/L. Preferably, the one or more additional microRNAs are present in a concentration of 10-1000 pmol/L. More preferably, the one or more additional microRNAs are present in a concentration of 100-1000 pmol/L.

In another aspect the present invention provides a nutritional composition of the present invention for use as a medicament.

In another related aspect the present invention provides a nutritional composition of the present invention for use in protecting gastrointestinal health in a subject, promoting growth and development (e.g. neuronal and epidermal development) in a subject, or reducing the risk of a subject developing infections, lymphoproliferative disorders, allergic diseases (e.g. allergic asthma), or inflammatory diseases.

In another related aspect the present invention provides a method of feeding a subject comprising administering to the subject a nutritional composition of the present invention.

In another related aspect the present invention provides a method of protecting gastrointestinal health in a subject, promoting growth and development (e.g. neuronal and epidermal development) in a subject, or reducing the risk of a subject developing infections, lymphoproliferative disorders, allergic diseases (e.g. allergic asthma), or inflammatory diseases, comprising administering to the subject a nutritional composition of the present invention.

In another aspect the present invention provides miR-3126 for use as a medicament. The miR-3126 may be in a nutritional composition of the present invention.

In another related aspect the present invention provides miR-3126 for use in protecting gastrointestinal health in a subject, promoting growth and development (e.g. neuronal and epidermal development) in a subject, or reducing the risk of a subject developing infections, lymphoproliferative disorders, allergic diseases (e.g. allergic asthma), or inflammatory diseases.

In another related aspect the present invention provides a method of feeding a subject comprising administering to the subject miR-3126.

In another related aspect the present invention provides a method of protecting gastrointestinal health in a subject, promoting growth and development (e.g. neuronal and epidermal development) in a subject, or reducing the risk of a subject developing infections, lymphoproliferative disorders, allergic diseases (e.g. allergic asthma), or inflammatory diseases. The miR-3126 may be in a nutritional composition of the present invention.

In preferred embodiments of these aspects of the present invention the subject is an infant. The infant may be 0-12 months old, 2-12 months old, 3-12 months old, 0-6 months old, 2-6 months old, or 3-6 months old. Preferably, the infant is 0-6 months old. More preferably, the infant is 2-6 months old. Most preferably, the infant is 3-6 months old.

In another aspect the present invention provides use of miR-3126 for providing a nutritional composition to mimic natural breast milk. The nutritional composition may be a nutritional composition according to the present invention.

In another aspect the present invention provides use of miR-3126 to modulate gene expression of one or more gene selected from: Ninein, Unc-13 homolog D, Sulfatase 2, IL-32, OXER1, TMEM127, Butyrophilin, Integrin subunit alpha 2, Integrin beta 1, tubulin alpha 4A, tubulin beta 6, tubulin beta 2A and tubulin beta 2B.

In another aspect the present invention provides a method of producing a nutritional composition of the present invention, comprising:

(i) providing a base nutritional composition; and (ii) adding miR-3126 to the base nutritional composition to provide a nutritional of the present invention.

DETAILED DESCRIPTION

Various preferred features and embodiments of the present invention will now be described by way of non-limiting examples.

It must be noted that as used herein and in the appended claims, the singular forms "a", "an", and "the" include plural referents unless the context clearly dictates otherwise.

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

As used herein the term "about" means approximately, in the region of, roughly, or around. When the term "about" is used in conjunction with a numerical value or range, it modifies that value or range by extending the boundaries above and below the numerical value(s) set forth. In general, the terms "about" and "approximately" are used herein to modify a numerical value(s) above and below the stated value(s) by 10%.

The publications discussed herein are provided solely for their disclosure prior to the filing date of the present application. Nothing herein is to be construed as an admission that such publications constitute prior art to the claims appended hereto.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

Nutritional Composition

In one aspect the present invention provides a nutritional composition comprising miR-3126.

According to the present invention, a "nutritional composition" means a composition which nourishes a subject. As used herein, the term "nutritional composition" does not include natural milk of human or animal origin, i.e. the nutritional composition is not natural human or animal milk. "Natural human milk" or "natural animal milk" refers to milk directly obtainable from a human or animal and does not encompass e.g. synthetic milk, infant formulas etc.

The nutritional composition of the present invention may comprise components derived from natural milk. For example, the nutritional composition of the present invention may comprise components derived from natural human milk and/or components derived from natural animal milk (e.g. bovine milk).

In a preferred embodiment of the invention, the nutritional composition contains miR-3126 as an active ingredient.

The nutritional composition is not particularly limited as long as it is suitable for administration (e.g. oral or intravenous administration). Examples of suitable nutritional compositions include foodstuffs, drinks, supplements, drug bases, and animal feeds.

Preferably, the nutritional composition according to the invention is suitable for infants. For example the nutritional composition may be an infant formula, a baby food, an infant cereal composition, a fortifier such as a human milk fortifier, or a supplement. Preferably, the nutritional composition is an infant formula, a fortifier, or a supplement.

In some embodiments the nutritional composition of the invention is a complete nutritional composition (fulfilling all or most of the nutritional needs of the subject). In other embodiments the nutrition composition is a supplement or a fortifier intended, for example, to supplement human milk or to supplement an infant formula.

The nutritional composition of the invention may be taken orally or intravenously, preferably orally.

The nutritional composition of the present invention can be in solid (e.g. powder), liquid or gelatinous form.

The nutritional composition according to the invention may be an enteral nutritional composition. An "enteral nutritional composition" is a foodstuff that involves the gastrointestinal tract for its administration.

The nutritional composition according to the invention may be a hypoallergenic nutritional composition. A "hypoallergenic" composition is a composition which is unlikely to cause allergic reactions.

The nutritional composition according to the invention may be prepared in any suitable manner.

Infant Formula

In preferred embodiments the nutritional composition is an infant formula.

The term "infant formula" may refer to a foodstuff intended for particular nutritional use by infants during the first year of life and satisfying by itself the nutritional requirements of this category of person, as defined in European Commission Regulation (EU) 2016/127 of 25 Sep. 2015. The term "infant formula" may also refer to a nutritional composition intended for infants and as defined in Codex Alimentarius (Codex STAN 72-1981).

The expression "infant formula" encompasses both "starter infant formula" and "follow-up formula" or "follow-on formula". In one embodiment the infant formula is a starter infant formula. In one embodiment the infant formula is a follow-up formula or follow-on formula. A "follow-up formula" or "follow-on formula" is given from the 6th month onwards. Infant formula constitutes the principal liquid element in the progressively diversified diet of this category of person.

Infants can be fed solely with infant formula or the infant formula can be used as a complement of human milk.

The infant formula of the invention may be in the form of a powder or liquid.

The liquid may be, for example, a concentrated liquid infant formula or a ready-to-feed infant formula. The infant formula may be in the form of a reconstituted infant formula (i.e. a liquid infant formula that has been reconstituted from a powdered form). The concentrated liquid infant formula is preferably capable of being diluted into a liquid composition suitable for feeding an infant, for example by the addition of water.

In one embodiment, the infant formula is in a powdered form. The powder is capable of being reconstituted into a liquid composition suitable for feeding an infant, for example by the addition of water.

The infant formula may have an energy density of about 60-72 kcal per 100 mL, when formulated as instructed. Suitably, the infant formula may have an energy density of about 60-70 kcal per 100 mL, when formulated as instructed.

Fortifier

In other preferred embodiments the nutritional composition is a fortifier.

The term "fortifier" may refer to liquid or solid nutritional compositions suitable for mixing with breast milk or infant formula.

The fortifier may be a milk fortifier. The term "milk fortifier", refers to any composition used to fortify or supplement either human breast milk or infant formula.

The fortifier may be, for example, 10-times concentrated, 15-times concentrated, 20-times concentrated, 25-times concentrated, 30-times concentrated, 35-times concentrated, 40-times concentrated, 45-times concentrated, 50-times concentrated, 60-times concentrated, 70-times concentrated, 80-times concentrated, 90-times concentrated, or 100-times concentrated, compared to the desired final concentration in the breast milk or infant formula.

Supplement

In other preferred embodiments the nutritional composition is a supplement.

A "supplement" or "dietary supplement" may be used to complement the nutrition of an individual (it is typically used as such but it might also be added to any kind of compositions intended to be ingested).

The supplement may be in the form of for example tablets, capsules, pastilles or a liquid. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

When the nutritional composition is a supplement, it may be provided in the form of unit doses.

Pharmaceutical Composition

In some embodiments the nutritional composition is a pharmaceutical composition.

The form of the pharmaceutical preparation is not particularly limited, and examples include tablet, pill, powder, solution, suspension, emulsion, granule, capsule, syrup, and so forth. Additives widely used as pharmaceutical carriers for oral administration such as excipients, binders, disintegrating agents, lubricants, stabilizers, corrigents, diluents, and surfactants can be used.

Examples of suitable binders include starch, gelatin, natural sugars such as glucose, anhydrous lactose, free-flow lactose, beta-lactose, corn sweeteners, natural and gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Components

The nutritional composition of the invention may contain a protein source, a carbohydrate source and/or a lipid source. In some embodiments however, especially if the nutritional composition of the invention is a supplement or a fortifier, there may be only lipids (or a lipid source).

Protein

The nutritional composition according to the present invention may contain a protein source.

The protein may be present in the nutritional composition of the present invention in any suitable amount. For example, the protein content of the nutritional composition of the invention may be in the range of from 1.6 to 3 g per 100 kcal, especially when the nutritional composition is an infant formula. In some embodiments, especially when the nutritional composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The protein source may be any protein source which is suitable for use in a nutritional composition. Protein sources based on, for example, whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. In some embodiments the protein source is whey predominant (i.e. more than 50% of proteins are coming from whey proteins, such as 60% or 70%).

The proteins may be intact or hydrolysed or a mixture of intact and hydrolysed proteins.

By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20), for example for infants or young children believed to be at risk of developing cow's milk allergy. The degree of hydrolysis (DH) of the protein can be between 2 and 20, or between 8 and 40, or between 20 and 60 or between 20 and 80 or more than 10, 20, 40, 60, 80 or 90. In one embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

Carbohydrate

The nutritional composition according to the present invention may contain a carbohydrate source.

The carbohydrate may be present in the nutritional composition of the present invention in any suitable amount. For example, the carbohydrate content of the nutritional composition of the invention may be in the range 9-14 g carbohydrate per 100 kcal, especially when the nutritional composition is an infant formula.

The carbohydrate source may be any carbohydrate source which is suitable for use in a nutritional composition. Some suitable carbohydrate sources include lactose, sucrose, saccharose, maltodextrin, starch and mixtures thereof may be used.

Fat

The nutritional composition according to the present invention may contain a source of lipids (fat).

The fat may be present in the nutritional composition of the present invention in any suitable amount. For example, the fat content of the nutritional composition of the invention may be in the range 4.0-6.0 g fat per 100 kcal, especially when the nutritional composition is an infant formula.

Example fats for use in the nutritional composition of the invention include sunflower oil, low erucic acid rapeseed oil, safflower oil, canola oil, olive oil, coconut oil, palm kernel oil, soybean oil, fish oil, palm oleic, high oleic sunflower oil and high oleic safflower oil, and microbial fermentation oil containing long chain, polyunsaturated fatty acids.

The fat may also be in the form of fractions derived from these oils, such as palm olein, medium chain triglycerides (MCT) and esters of fatty acids such as arachidonic acid, linoleic acid, palmitic acid, stearic acid, docosahexaeonic acid, linolenic acid, oleic acid, lauric acid, capric acid, caprylic acid, caproic acid, and the like.

Further example fats include structured lipids (i.e. lipids that are modified chemically or enzymatically in order to change their structure). Preferably, the structured lipids are sn2 structured lipids, for example comprising triglycerides having an elevated level of palmitic acid at the sn2 position of the triglyceride. Structured lipids may be added or may be omitted.

Oils containing high quantities of preformed arachidonic acid (ARA) and/or docosahexaenoic acid (DHA), such as fish oils or microbial oils, may be added.

Long chain polyunsaturated fatty acids, such as dihomo-γ-linolenic acid, arachidonic acid (ARA), eicosapentaenoic acid and docosahexaenoic acid (DHA), may also be added.

The essential fatty acids linoleic and a-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

Further Components

The nutritional composition of the invention may also contain any suitable vitamins and minerals.

For example, the nutritional composition of the invention may contain all vitamins and minerals understood to be essential in the daily diet and in nutritionally significant amounts. Minimum requirements have been established for certain vitamins and minerals. Examples of minerals, vitamins and other nutrients optionally present in the nutritional composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

The nutritional composition of the invention may contain emulsifiers and stabilisers such as soy, lecithin, citric acid esters of mono- and diglycerides, and the like.

The nutritional composition of the invention may also contain one or more carotenoid. In some particular embodiments of the invention, the nutritional composition of the invention does not comprise any carotenoids.

The nutritional composition of the invention may also contain other substances which may have a beneficial effect such as lactoferrin, osteopontin, TGFbeta, slgA, glutamine, nucleotides, nucleosides, and the like.

The nutritional composition of the invention can further comprise at least one non-digestible oligosaccharide (e.g. prebiotics).

Examples of prebiotics may be fructooligosaccharide, galactooligosaccharide, acidic oligosaccharides, human milk oligosaccharide (HMO), or bovine's milk oligosaccharide (BMO) like cow's milk oligosaccharide (CMO) such as "CMOS-GOS". Some examples are N-acetylated oligosaccharides, sialylated oligosaccharides, fucosylated oligosaccharides and any mixtures thereof.

The nutritional composition of the present invention can further comprise at least one probiotic (or probiotic strain), such as a probiotic bacterial strain. The term "probiotic" refers to microbial cell preparations or components of microbial cells with beneficial effects on the health or well-being of the host. In particular, probiotics may improve gut barrier function.

Preferred probiotics are those which as a whole are safe, are L (+) lactic acid producing cultures and have acceptable shelf-life for products that are required to remain stable and effective for up to 24 months.

Examples of probiotic micro-organisms for use in the nutritional composition of the present invention include yeasts, such as *Saccharomyces, Debaromyces, Candida, Pichia* and *Torulopsis*; and bacteria, such as the genera *Bifidobacterium, Bacteroides, Clostridium, Fusobacterium,*

*Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus.*

Specific examples of suitable probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei* Shirota, *Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus rhamnosus* (*Lactobacillus* GG), *Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus* and *Staphylococcus xylosus.* microRNAs

MicroRNAs (miRNAs) are small, non-coding RNAs around 17-25 nucleotides in length. They are regulatory RNA molecules that function to regulate the activity of specific mRNA targets.

Mature miRNA is denoted by the prefix "miR" followed by a dash and a number. Uncapitalized "mir-" refers to the pre-miRNA and the pri-miRNA. "MIR" refers to the human gene that encodes the miRNA.

In the present invention, mature miRNA is preferably used. However, the present invention may also be carried out using pre-miRNA and/or pri-miRNA. Mature miRNA can be obtained by digesting pre-miRNA and/or pri-miRNA with a Dicer enzyme (e.g. Dicer1) or the like, which occur naturally in humans and animals. Accordingly, whilst mature miRNA is generally referred to (e.g. miR-3126), pre-miRNA and/or pri-miRNA (e.g. pri-miR-3126) could also be used in the present invention (e.g. in combination with mature miRNA or instead of mature miRNA). Thus, the mature miRNA referred to herein may be replaced with corresponding pre-miRNA and/or pri-miRNA.

Species of origin is designated with a three-letter prefix, e.g., hsa-miR-124 is a human (*Homo sapiens*) miRNA and oar-miR-124 is a sheep (*Ovis aries*) miRNA.

When two mature microRNAs originate from opposite arms of the same pre-miRNA and are found in roughly similar amounts, they are denoted with a -3p or -5p suffix. If the mature microRNA found from one arm of the hairpin is much more abundant than that found from the other arm, an asterisk following the name indicates the mature species found at low levels from the opposite arm of a hairpin. For example, miR-124 and miR-124* share a pre-miRNA hairpin, but much more miR-124 is found in the cell.

miRNA sequences have been deposited in miRBase database at www.mirbase.org. The miRBase database is a searchable database of published miRNA sequences and annotation.

miR-3126

The present inventors have found that miR-3126 is present in natural breast milk. In particular, the present inventors have found that expression of miR-3126 in natural breast milk increases between two weeks and three months post-partum.

Accordingly, in one aspect the present invention provides use of miR-3126 for providing a nutritional composition. In particular, the present invention provides use of miR-3126 for providing a nutritional composition to mimic natural breast milk (e.g. human breast milk). The nutritional composition may be a nutritional composition according to the present invention.

miR-3126 is also known as MicroRNA 3126 and is from the MIPF0001525 or mir-3126 gene family. hsa-mir-3126 has accession number MI0014143.

The miR-3126 for use in the present invention may comprise or consist of miR-3126-5p and/or miR-3126-3p. Preferably, the miR-3126 comprises miR-3126-5p. For example, at least 50%, at least 60%, at least 70%, at least 80%, at least 90%, at least 95%, at least 99% or 100% of the miR-3126 may be miR-3126-5p. More preferably, the miR-3126 consists of miR-3126-5p.

The miR-3126 for use in the present invention may be human miR-3126, i.e. hsa-miR-3126. The miR-3126 for use in the present invention may comprise or consist of hsa-miR-3126-5p and/or hsa-miR-3126-3p. Preferably, the miR-3126 comprises hsa-miR-3126-5p. For example, at least 50%, at least 60%, at least 70%, at least 80%, at least 90%, at least 95%, at least 99% or 100% of the miR-3126 may be hsa-miR-3126-5p. More preferably, the miR-3126 consists of hsa-miR-3126-5p.

An illustrative sequence for hsa-mir-3126 (i.e. the pre-miRNA from which hsa-miR-3126 is derived) is shown below as SEQ ID NO: 1. The miR-3126 for use in the present invention may be derived from pre-miRNA comprising or consisting of a sequen ce which has at least 20%, at least 30%, at least 50%, at least 60%, at least 70%, at least 80%, at least 85%, at least 90%, at least 95%, or 100% identity to SEQ ID NO: 1. Preferably, the miR-3126 for use in the present invention is derived from pre-miRNA comprising of consisting of a sequence which has at least 95% identity to SEQ ID NO: 1. More preferably, the miR-3126 for use in the present invention is derived from pre-miRNA comprising of consisting of a sequence according to SEQ ID NO: 1.

illustrative hsa-mir-3126 sequence

SEQ ID NO: 1

AUGAUUAUAUGAGGGACAGAUGCCAGAAGCACUGGUUAUGAUUUGCAUC

UGGCAUCCGUCACACAGAUAAUUAU

An illustrative sequence for hsa-miR-3126-5p (i.e. mature miRNA) is shown below as SEQ ID NO: 2. The miR-3126 for use in the present invention may comprise or consist of a sequence which has at least 80%, at least 85%, at least 90%, at least 95%, or 100% identity to SEQ ID NO: 2. Preferably, the miR-3126 for use in the present invention comprises or consists of a sequence which has at least 95% identity to SEQ ID NO: 2. More preferably, the miR-3126 for use in the present invention comprises or consists of a sequence according to SEQ ID NO: 2.

illustrative hsa-miR-3126-5p sequence

SEQ ID NO: 2

UGAGGGACAGAUGCCAGAAGCA

An illustrative sequence for hsa-miR-3126-3p (i.e. mature miRNA) is shown below as SEQ ID NO: 3. The miR-3126 for use in the present invention may comprise or consist of a sequence which has at least 80%, at least 85%, at least 90%, at least 95%, at least 98%, at least 99%, or 100% identity to SEQ ID NO: 3. Preferably, the miR-3126 for use in the present invention comprises or consists of a sequence which has at least 95% identity to SEQ ID NO: 2. More preferably, the miR-3126 for use in the present invention comprises or consists of a sequence according to SEQ ID NO: 3.

```
illustrative hsa-miR-3126-3p sequence
                                        SEQ ID NO: 3
CAUCUGGCAUCCGUCACACAGA
```

The miR-3126 may be present in the nutritional composition of the present invention in a concentration of 0.1-10000 pmol/L, 0.1-1000 pmol/L, 1-1000 pmol/L, 10-1000 pmol/L, or 100-1000 pmol/L, especially when the nutritional composition is an infant formula. Preferably, the miR-3126 is present in the nutritional composition of the present invention in a concentration of 10-1000 pmol/L, especially when the nutritional composition is an infant formula. More preferably, the miR-3126 is present in the nutritional composition of the present invention in a concentration of 100-1000 pmol/L, especially when the nutritional composition is an infant formula. The miR-3126 may be present in the nutritional composition of the present invention such that the concentration is about the same as in natural breast milk.

When the nutritional composition is a fortifier, the miR-3126 may be present in the fortifier such that after mixing with breast milk or infant formula the concentration of miR-3126 is 0.1-10000 pmol/L, 0.1-1000 pmol/L, 1-1000 pmol/L, 10-1000 pmol/L, or 100-1000 pmol/L. Preferably, the miR-3126 is present in the fortifier such that after mixing with breast milk or infant formula the concentration of miR-3126 is 10-1000 pmol/L. More preferably, the miR-3126 is present in the fortifier such that after mixing with breast milk or infant formula the concentration of miR-3126 is 100-1000 pmol/L. The miR-3126 may be present in the fortifier such that after mixing with breast milk or infant formula the concentration of miR-3126 is about the same as in natural breast milk.

When the nutritional composition is a supplement, the miR-3126 may be present in the supplement such that a unit dose is provided. Thus, the supplement may provide a miR-3126 dose equivalent to 50-250 ml, 100-250 ml, 150-250 ml, or about 100 ml, or about 200 ml of natural breast milk. For example, miR-3126 may be present in the supplement in an amount of 0.02-2000 pmol, 0.02-200 pmol, 0.2-200 pmol, 2-200 pmol, or 20-200 pmol. Preferably, miR-3126 is present in the supplement in an amount of 2-200 pmol. More preferably, miR-3126 is present in the supplement in an amount of 20-200 pmol.

The nutritional composition of the present invention preferably comprises hsa-miR-3126-5p in a concentration of 10-1000 pmol/L, especially when the nutritional composition is an infant formula. The nutritional composition of the present invention more preferably comprises hsa-miR-3126-5p in a concentration of 100-1000 pmol/L, especially when the nutritional composition is an infant formula.

When the nutritional composition is in a powder form capable of being reconstituted into a liquid composition, the concentration of miR-3126 is based on the reconstituted liquid composition.

Other miRNAs

The nutritional composition of the present invention may comprise one or more microRNAs in addition to miR-3126.

For example, the nutritional composition may comprise one or more additional microRNAs which are abundant in natural breast milk. Suitable additional miRNAs which are abundant in natural breast milk include: let-7b, let-7c, miR-19b, miR-22, miR-24, miR-25, miR-29a, miR-30a, miR-92a, miR-99a, miR-100, miR-197, miR-30d, miR-181a, miR-181b, miR-205, miR-210, miR-221, miR-125b, miR-125a, miR-149, miR-193a, miR-320a, miR-200a, miR-99b, miR-130b, miR-30e, miR-375, miR-378a, miR-151a, miR-425, miR-484, miR-146b, miR-574, miR-652, miR-320c, miR-3141, let-7d, miR-196a, miR-187, miR-516a, miR-92b, and miR-3184.

The nutritional composition may comprise one or more additional microRNAs selected from: let-7b, let-7c, miR-19b, miR-22, miR-24, miR-25, miR-29a, miR-30a, miR-92a, miR-99a, miR-100, miR-197, miR-30d, miR-181a, miR-181b, miR-205, miR-210, miR-221, miR-125b, miR-125a, miR-149, miR-193a, miR-320a, miR-200a, miR-99b, miR-130b, miR-30e, miR-375, miR-378a, miR-151a, miR-425, miR-484, miR-146b, miR-574, miR-652, miR-320c, and miR-3141.

The nutritional composition may comprise one or more additional microRNAs selected from: let-7d, miR-196a, miR-187, miR-516a, miR-92b, and miR-3184.

In one embodiment the nutritional composition comprises miR-3184 and/or miR-3141. In another embodiment the nutritional composition comprises miR-3184.

The one or more additional microRNAs for use in the present invention may comprise or consist of human or bovine microRNAs. Preferably the one or more additional microRNAs are human microRNAs.

The one or more additional microRNAs for use in the present invention may comprise or consist of both mature microRNAs originating from opposite arms of the same pre-miRNA. Preferably, the one or more additional microRNAs for use in the present invention comprise or consist of a mature microRNA from one arm of the hairpin, for example the mature microRNA which is most abundant in natural breast milk.

The nutritional composition may comprise one or more additional microRNAs selected from: hsa-let-7b-5p, hsa-let-7c-5p, hsa-miR-19b-3p, hsa-miR-22-3p, hsa-miR-24-3p, hsa-miR-25-3p, hsa-miR-29a-3p, hsa-miR-30a-5p, hsa-miR-92a-3p, hsa-miR-99a-5p, hsa-miR-100-5p, hsa-miR-197-3p, hsa-miR-30d-5p, hsa-miR-181a-5p, hsa-miR-181b-5p, hsa-miR-205-5p, hsa-miR-210-3p, hsa-miR-221-3p, hsa-miR-125b-5p, hsa-miR-125a-5p, hsa-miR-149-3p, hsa-miR-193a-5p, hsa-miR-193a-3p, hsa-miR-320a, hsa-miR-200a-3p, hsa-miR-99b-5p, hsa-miR-130b-3p, hsa-miR-30e-5p, hsa-miR-375, hsa-miR-378a-3p, hsa-miR-151a-3p, hsa-miR-425-5p, hsa-miR-484, hsa-miR-146b-5p, hsa-miR-574-5p, hsa-miR-652-3p, hsa-miR-320c, hsa-miR-3141, hsa-let-7d-3p, hsa-miR-196a-5p, hsa-miR-187-5p, hsa-miR-516a-5p, hsa-miR-92b-5p, hsa-miR-3184-3p, bta-let-7b, bta-let-7c, bta-miR-19b, bta-miR-22-3p, bta-miR-24-3p, bta-miR-25, bta-miR-29a, bta-miR-30a-5p, bta-miR-92a, bta-miR-99a-5p, bta-miR-100, bta-miR-197, bta-miR-30d, bta-miR-181a, bta-miR-181b, bta-miR-205, bta-miR-210, bta-miR-221, bta-miR-125b, bta-miR-125a, bta-miR-149-3p, bta-miR-193a-5p, bta-miR-193a-3p, bta-miR-320a, bta-miR-200a, bta-miR-99b, bta-miR-130b, bta-miR-30e-5p, bta-miR-375, bta-miR-378, bta-miR-151-3p, bta-miR-425-5p, bta-miR-484, bta-miR-146b, bta-miR-574, bta-miR-652, bta-miR-320b, bta-miR-3141, bta-let-7d, bta-miR-196a-5p, bta-miR-187-5p, and bta-miR-92b-5p.

The nutritional composition may comprise one or more additional microRNAs selected from: hsa-let-7b-5p, hsa-let-7c-5p, hsa-miR-19b-3p, hsa-miR-22-3p, hsa-miR-24-3p, hsa-miR-25-3p, hsa-miR-29a-3p, hsa-miR-30a-5p, hsa-miR-92a-3p, hsa-miR-99a-5p, hsa-miR-100-5p, hsa-miR-197-3p, hsa-miR-30d-5p, hsa-miR-181a-5p, hsa-miR-181b-5p, hsa-miR-205-5p, hsa-miR-210-3p, hsa-miR-221-3p, hsa-miR-125b-5p, hsa-miR-125a-5p, hsa-miR-149-3p, hsa-miR-193a-5p, hsa-miR-193a-3p, hsa-miR-320a, hsa-miR-200a-3p, hsa-miR-99b-5p, hsa-miR-130b-3p, hsa-miR-30e-5p, hsa-miR-375, hsa-miR-378a-3p, hsa-miR-151a-3p, hsa-miR-425-5p, hsa-miR-484, hsa-miR-146b-5p, hsa-miR-574-5p, hsa-miR-652-3p, hsa-miR-320c, hsa-miR-3141, hsa-let-7d-3p, hsa-miR-196a-5p, hsa-miR-187-5p, hsa-miR-516a-5p, hsa-miR-92b-5p, hsa-miR-3184-3p.

The nutritional composition may comprise one or more additional microRNAs selected from: hsa-let-7b-5p, hsa-let-7c-5p, hsa-miR-19b-3p, hsa-miR-22-3p, hsa-miR-24-3p, hsa-miR-25-3p, hsa-miR-29a-3p, hsa-miR-30a-5p, hsa-miR-92a-3p, hsa-miR-99a-5p, hsa-miR-100-5p, hsa-miR-197-3p, hsa-miR-30d-5p, hsa-miR-181a-5p, hsa-miR-181b-5p, hsa-miR-205-5p, hsa-miR-210-3p, hsa-miR-221-3p, hsa-miR-125b-5p, hsa-miR-125a-5p, hsa-miR-149-3p, hsa-miR-193a-5p, hsa-miR-193a-3p, hsa-miR-320a, hsa-miR-200a-3p, hsa-miR-99b-5p, hsa-miR-130b-3p, hsa-miR-30e-5p, hsa-miR-375, hsa-miR-378a-3p, hsa-miR-151a-3p, hsa-miR-425-5p, hsa-miR-484, hsa-miR-146b-5p, hsa-miR-574-5p, hsa-miR-652-3p, hsa-miR-320c, hsa-miR-3141, bta-let-7b, bta-let-7c, bta-miR-19b, bta-miR-22-3p, bta-miR-24-3p, bta-miR-25, bta-miR-29a, bta-miR-30a-5p, bta-miR-92a, bta-miR-99a-5p, bta-miR-100, bta-miR-197, bta-miR-30d, bta-miR-181a, bta-miR-181b, bta-miR-205, bta-miR-210, bta-miR-221, bta-miR-125b, bta-miR-125a, bta-miR-149-3p, bta-miR-193a-5p, bta-miR-193a-3p, bta-miR-320a, bta-miR-200a, bta-miR-99b, bta-miR-130b, bta-miR-30e-5p, bta-miR-375, bta-miR-378, bta-miR-151-3p, bta-miR-425-5p, bta-miR-484, bta-miR-146b, bta-miR-574, bta-miR-652, bta-miR-320b, and bta-miR-3141.

The nutritional composition may comprise one or more additional microRNAs selected from: hsa-let-7b-5p, hsa-let-7c-5p, hsa-miR-19b-3p, hsa-miR-22-3p, hsa-miR-24-3p, hsa-miR-25-3p, hsa-miR-29a-3p, hsa-miR-30a-5p, hsa-miR-92a-3p, hsa-miR-99a-5p, hsa-miR-100-5p, hsa-miR-197-3p, hsa-miR-30d-5p, hsa-miR-181a-5p, hsa-miR-181b-5p, hsa-miR-205-5p, hsa-miR-210-3p, hsa-miR-221-3p, hsa-miR-125b-5p, hsa-miR-125a-5p, hsa-miR-149-3p, hsa-miR-193a-5p, hsa-miR-193a-3p, hsa-miR-320a, hsa-miR-200a-3p, hsa-miR-99b-5p, hsa-miR-130b-3p, hsa-miR-30e-5p, hsa-miR-375, hsa-miR-378a-3p, hsa-miR-151a-3p, hsa-miR-425-5p, hsa-miR-484, hsa-miR-146b-5p, hsa-miR-574-5p, hsa-miR-652-3p, hsa-miR-320c, and hsa-miR-3141.

The nutritional composition may comprise one or more additional microRNAs selected from: hsa-let-7d-3p, hsa-miR-196a-5p, hsa-miR-187-5p, hsa-miR-516a-5p, hsa-miR-92b-5p, hsa-miR-3184-3p, bta-let-7d, bta-miR-196a-5p, bta-miR-187-5p, and bta-miR-92b-5p.

The nutritional composition may comprise one or more additional microRNAs selected from: hsa-let-7d-3p, hsa-miR-196a-5p, hsa-miR-187-5p, hsa-miR-516a-5p, hsa-miR-92b-5p, and hsa-miR-3184-3p.

In one embodiment, the nutritional composition comprises hsa-miR-3184-3p and/or hsa-miR-3141. In another embodiment, the nutritional composition comprises hsa-miR-3184-3p.

Illustrative sequences for suitable additional microRNAs are shown in Table 1 below.

TABLE 1

Illustrative microRNA sequences

| Human miRNA | Illustrative sequence | Bovine miRNA | Illustrative sequence |
|---|---|---|---|
| hsa-let-7b-5p | UGAGGUAGUAGGUUGUG UGGUU (SEQ ID NO: 4) | bta-let-7b | UGAGGUAGUAGGUUGUG UGGUU (SEQ ID NO: 49) |
| hsa-let-7c-5p | UGAGGUAGUAGGUUGUA UGGUU (SEQ ID NO: 5) | bta-let-7c | UGAGGUAGUAGGUUGUA UGGUU (SEQ ID NO: 50) |
| hsa-miR-19b-3p | UGUGCAAAUCCAUGCAAA ACUGA (SEQ ID NO: 6) | bta-miR-19b | UGUGCAAAUCCAUGCAAA ACUGA (SEQ ID NO: 51) |
| hsa-miR-22-3p | AAGCUGCCAGUUGAAGA ACUGU (SEQ ID NO: 7) | bta-miR-22-3p | AAGCUGCCAGUUGAAGAA CUG (SEQ ID NO: 52) |
| hsa-miR-24-3p | UGGCUCAGUUCAGCAGG AACAG (SEQ ID NO: 8) | bta-miR-24-3p | UGGCUCAGUUCAGCAGG AACAG (SEQ ID NO: 53) |
| hsa-miR-25-3p | CAUUGCACUUGUCUCGG UCUGA (SEQ ID NO: 9) | bta-miR-25 | CAUUGCACUUGUCUCGG UCUGA (SEQ ID NO: 54) |
| hsa-miR-29a-3p | UAGCACCAUCUGAAAUC GGUUA (SEQ ID NO: 10) | bta-miR-29a | CUAGCACCAUCUGAAAUC GGUUA (SEQ ID NO: 55) |
| hsa-miR-30a-5p | UGUAAACAUCCUCGACU GGAAG (SEQ ID NO: 11) | bta-miR-30a-5p | UGUAAACAUCCUCGACUG GAAGCU (SEQ ID NO: 56) |
| hsa-miR-92a-3p | UAUUGCACUUGUCCCGG CCUGU (SEQ ID NO: 12) | bta-miR-92a | UAUUGCACUUGUCCCGG CCUGU (SEQ ID NO: 57) |

TABLE 1-continued

| Illustrative microRNA sequences | | | |
|---|---|---|---|
| Human miRNA | Illustrative sequence | Bovine miRNA | Illustrative sequence |
| hsa-miR-99a-5p | AACCCGUAGAUCCGAUC UUGUG (SEQ ID NO: 13) | bta-miR-99a-5p | AACCCGUAGAUCCGAUCU UGU (SEQ ID NO: 58) |
| hsa-miR-100-5p | AACCCGUAGAUCCGAAC UUGUG (SEQ ID NO: 14) | bta-miR-100 | AACCCGUAGAUCCGAACU UGUG (SEQ ID NO: 59) |
| hsa-miR-197-3p | UUCACCACCUUCUCCAC CCAGC (SEQ ID NO: 15) | bta-miR-197 | UUCACCACCUUCUCCACC CAGC (SEQ ID NO: 60) |
| hsa-miR-30d-5p | UGUAAACAUCCCCGACU GGAAG (SEQ ID NO: 16) | bta-miR-30d | UGUAAACAUCCCCGACUG GAAGCU (SEQ ID NO: 61) |
| hsa-miR-181a-5p | AACAUUCAACGCUGUCG GUGAGU (SEQ ID NO: 17) | bta-miR-181a | AACAUUCAACGCUGUCGG UGAGUU (SEQ ID NO: 62) |
| hsa-miR-181b-5p | AACAUUCAUUGCUGUCG GUGGGU (SEQ ID NO: 18) | bta-miR-181b | AACAUUCAUUGCUGUCGG UGGGUU (SEQ ID NO: 63) |
| hsa-miR-205-5p | UCCUUCAUUCCACCGGA GUCUG (SEQ ID NO: 19) | bta-miR-205 | UCCUUCAUUCCACCGGAG UCUG (SEQ ID NO: 64) |
| hsa-miR-210-3p | CUGUGCGUGUGACAGCG GCUGA (SEQ ID NO: 20) | bta-miR-210 | ACUGUGCGUGUGACAGC GGCUGA (SEQ ID NO: 65) |
| hsa-miR-221-3p | AGCUACAUUGUCUGCUG GGUUUC (SEQ ID NO: 21) | bta-miR-221 | AGCUACAUUGUCUGCUG GGUUU (SEQ ID NO: 66) |
| hsa-miR-125b-5p | UCCCUGAGACCCUAACU UGUGA (SEQ ID NO: 22) | bta-miR-125b | UCCCUGAGACCCUAACUU GUGA (SEQ ID NO: 67) |
| hsa-miR-125a-5p | UCCCUGAGACCCUUUAA CCUGUGA (SEQ ID NO: 23) | bta-miR-125a | UCCCUGAGACCCUUUAAC CUGUG (SEQ ID NO: 68) |
| hsa-miR-149-3p | AGGGAGGGACGGGGGCU GUGC (SEQ ID NO: 24) | bta-miR-149-3p | GAGGGAGGGACGGGGGC UGUGC (SEQ ID NO: 69) |
| hsa-miR-193a-5p | UGGGUCUUUGCGGGCGA GAUGA (SEQ ID NO: 25) | bta-miR-193a-5p | UGGGUCUUUGCGGGCGA GAUGA (SEQ ID NO: 70) |
| hsa-miR-193a-3p | AACUGGCCUACAAAGUC CCAGU (SEQ ID NO: 26) | bta-miR-193a-3p | AACUGGCCUACAAAGUCC CAGU (SEQ ID NO: 71) |
| hsa-miR-320a | AAAAGCUGGGUUGAGAG GGCGA (SEQ ID NO: 27) | bta-miR-320a | AAAAGCUGGGUUGAGAG GGCGA (SEQ ID NO: 72) |
| hsa-miR-200a-3p | UAACACUGUCUGGUAAC GAUGU (SEQ ID NO: 28) | bta-miR-200a | UAACACUGUCUGGUAACG AUGUU (SEQ ID NO: 73) |
| hsa-miR-99b-5p | CACCCGUAGAACCGACC UUGCG (SEQ ID NO: 29) | bta-miR-99b | CACCCGUAGAACCGACCU UGCG (SEQ ID NO: 74) |
| hsa-miR-130b-3p | CAGUGCAAUGAUGAAAG GGCAU (SEQ ID NO: 30) | bta-miR-130b | CAGUGCAAUGAUGAAAGG GCAU (SEQ ID NO: 75) |
| hsa-miR-30e-5p | UGUAAACAUCCUUGACU GGAAG (SEQ ID NO: 31) | bta-miR-30e-5p | UGUAAACAUCCUUGACUG GAAGCU (SEQ ID NO: 76) |

TABLE 1-continued

| Illustrative microRNA sequences | | | |
|---|---|---|---|
| Human miRNA | Illustrative sequence | Bovine miRNA | Illustrative sequence |
| hsa-miR-375 | UUUGUUCGUUCGGCUCG CGUGA (SEQ ID NO: 32) | bta-miR-375 | UUUUGUUCGUUCGGCUC GCGUGA (SEQ ID NO: 77) |
| hsa-miR-378a-3p | ACUGGACUUGGAGUCAG AAGGC (SEQ ID NO: 33) | bta-miR-378 | ACUGGACUUGGAGUCAGA AGGC (SEQ ID NO: 78) |
| hsa-miR-151a-3p | CUAGACUGAAGCUCCUU GAGG (SEQ ID NO: 34) | bta-miR-151-3p | CUAGACUGAAGCUCCUUG AGG (SEQ ID NO: 79) |
| hsa-miR-425-5p | AAUGACACGAUCACUCCC GUUGA (SEQ ID NO: 35) | bta-miR-425-5p | AUGACACGAUCACUCCCG UUGA (SEQ ID NO: 80) |
| hsa-miR-484 | UCAGGCUCAGUCCCCUC CCGAU (SEQ ID NO: 36) | bta-miR-484 | UCAGGCUCAGUCCCCUCC CGAU (SEQ ID NO: 81) |
| hsa-miR-146b-5p | UGAGAACUGAAUUCCAUA GGCU (SEQ ID NO: 37) | bta-miR-146b | UGAGAACUGAAUUCCAUA GGCUGU (SEQ ID NO: 82) |
| hsa-miR-574-5p | UGAGUGUGUGUGUGUGA GUGUGU (SEQ ID NO: 38) | bta-miR-574 | UGAGUGUGUGUGUGUGA GUGUGUG (SEQ ID NO: 83) |
| hsa-miR-652-3p | AAUGGCGCCACUAGGGU UGUG (SEQ ID NO: 39) | bta-miR-652 | AAUGGCGCCACUAGGGU UGUG (SEQ ID NO: 84) |
| hsa-miR-320c | AAAAGCUGGGUUGAGAG GGU (SEQ ID NO: 40) | bta-miR-320b | AGCUGGGUUGAGAGGGU GGU (SEQ ID NO: 85) |
| hsa-miR-3141 | GAGGGCGGGUGGAGGAG GA (SEQ ID NO: 41) | bta-miR-3141 | GAGGGCGGGUGGAGGAG G (SEQ ID NO: 86) |
| hsa-miR-4478 | GAGGCUGAGCUGAGGAG (SEQ ID NO: 42) | NA | NA |
| hsa-let-7d-3p | CUAUACGACCUGCUGCC UUUCU (SEQ ID NO: 43) | bta-let-7d | AGAGGUAGUAGGUUGCA UAGUU (SEQ ID NO: 87) |
| hsa-miR-196a-5p | UAGGUAGUUUCAUGUUG UUGGG (SEQ ID NO: 44) | bta-miR-196a-5p | UAGGUAGUUUCAUGUUG UUGGG (SEQ ID NO: 88) |
| hsa-miR-187-5p | GGCUACAACACAGGACC CGGGC (SEQ ID NO: 45) | bta-miR-187-5p | UCGUGUCUUGUGUUGCA GCCGG (SEQ ID NO: 89) |
| hsa-miR-516a-5p | UUCUCGAGGAAAGAAGC ACUUUC (SEQ ID NO: 46) | NA | NA |
| hsa-miR-92b-5p | AGGGACGGGACGCGGUG CAGUG (SEQ ID NO: 47) | bta-miR-92b-5p | UAUUGCACUCGUCCCGG CCUCC (SEQ ID NO: 90) |
| hsa-miR-3184-3p | AAAGUCUCGCUCUCUGC CCCUCA (SEQ ID NO: 48) | NA | NA |

The nutritional composition may comprise one or more additional microRNAs with at least 80%, at least 85%, at least 90%, at least 95%, or 100% identity to any one of SEQ ID NOs: 4-90. The nutritional composition may comprise one or more additional microRNAs which have a sequence according to SEQ ID NOs: 4-90 given in table 1.

The nutritional composition may comprise one or more additional microRNAs with at least 80%, at least 85%, at least 90%, at least 95%, or 100% identity to any one of SEQ ID NOs: 4-42 or 49-86. The nutritional composition may comprise one or more additional microRNAs which have a sequence according to SEQ ID NOs: 4-42 or 49-86 given in table 1.

The nutritional composition may comprise one or more additional microRNAs with at least 80%, at least 85%, at least 90%, at least 95%, or 100% identity to any one of SEQ ID NOs: 4-42. The nutritional composition may comprise one or more additional microRNAs which have a sequence according to SEQ ID NOs: 4-42 given in table 1.

The nutritional composition may comprise one or more additional microRNAs with at least 80%, at least 85%, at least 90%, at least 95%, or 100% identity to any one of SEQ ID NOs: 43-48 or 87-90. The nutritional composition may comprise one or more additional microRNAs which have a sequence according to SEQ ID NOs: 43-48 or 87-90 given in table 1.

The nutritional composition may comprise one or more additional microRNAs with at least 80%, at least 85%, at least 90%, at least 95%, or 100% identity to any one of SEQ ID NOs: 43-48. The nutritional composition may comprise one or more additional microRNAs which have a sequence according to SEQ ID NOs: 43-48 given in table 1.

The nutritional composition may comprise a microRNA with at least 80%, at least 85%, at least 90%, at least 95%, or 100% identity to SEQ ID NO: 41 or 48. Preferably, the nutritional composition comprises a microRNA which has a sequence according to SEQ ID NO: 41 or 48. More preferably, the nutritional composition comprises a microRNA which has a sequence according to SEQ ID NO: 48.

Each of the one or more additional microRNAs may be present in the nutritional composition of the present invention in a concentration of 0.1-10000 pmol/L, 0.1-1000 pmol/L, 1-1000 pmol/L, 10-1000 pmol/L, or 100-1000 pmol/L, especially when the nutritional composition is an infant formula. Preferably, each of the one or more additional microRNAs are present in the nutritional composition of the present invention in a concentration of 10-1000 pmol/L, especially when the nutritional composition is an infant formula. More preferably, each of the one or more additional microRNAs are present in the nutritional composition of the present invention in a concentration of 100-1000 pmol/L, especially when the nutritional composition is an infant formula. The one or more additional microRNAs may be present in the nutritional composition of the present invention such that the concentration of each of the one or more additional microRNAs is about the same as in natural breast milk.

When the nutritional composition is a fortifier, each of the one or more additional microRNAs may be present in the fortifier such that after mixing with breast milk or infant formula the concentration of each of the one or more additional microRNAs is 0.1-10000 pmol/L, 0.1-1000 pmol/L, 1-1000 pmol/L, 10-1000 pmol/L, or 100-1000 pmol/L. Preferably, each of the one or more additional microRNAs are present in the fortifier such that after mixing with breast milk or infant formula the concentration of each of the one or more additional microRNAs is 10-1000 pmol/L. More preferably, the each of the one or more additional microRNAs is present in the fortifier such that after mixing with breast milk or infant formula the concentration of each of the one or more additional microRNAs is 100-1000 pmol/L. The one or more additional microRNAs may be present in the fortifier such that after mixing with breast milk or infant formula the concentration of each of the one or more additional microRNAs is about the same as in natural breast milk.

When the nutritional composition is a supplement, each of the one or more additional microRNAs may be present in the fortifier such that supplement such that a unit dose of each microRNA is provided. Thus, the supplement may provide a dose equivalent to 50-250 ml, 100-250 ml, 150-250 ml, or about 100 ml, or about 200 ml of natural breast milk. For example, each of the one or more additional microRNAs may be present in the supplement in an amount of 0.02-2000 nmol, 0.02-200 nmol, 0.2-200 nmol, 2-200 nmol, or 20-200 nmol. Preferably, each of the one or more additional microRNAs is present in the supplement in an amount of 2-200 nmol. More preferably, each of the one or more additional microRNAs is present in the supplement in an amount of 20-200 nmol.

When the nutritional composition is in a powder form capable of being reconstituted into a liquid composition, the concentration of each of the one or more additional microRNAs is based on the reconstituted liquid composition.

Preparation of miRNAs miRNAs for use in the present invention can be obtained by any suitable method known in the art.

miRNAs may be prepared synthetically or isolated from a body fluid.

Mature miRNA can be prepared synthetically by preparing a partially double-stranded RNA as a precursor of miRNA (pre-miRNA), and digesting it with a Dicer enzyme. As the Dicer enzyme, commercially available enzymes can be used. Double-stranded RNA (e.g. pre-miRNA) can be prepared by, for example, a RNA polymerase reaction using a double-stranded DNA having a complementary sequence as a template. Double-stranded DNA can be prepared by amplification based on PCR using a chromosomal DNA of mammal as a template and primers designed so as to be able to amplify the sequence of miRNA.

Further, miRNA can also be prepared by chemical synthesis. That is, miRNA can be obtained by synthesizing a sense strand and an antisense strand and annealing them.

miRNA may be isolated from colostrum or breast milk. miRNA may be isolated from colostrum or breast milk of bovine origin.

Variants and Fragments

In addition to the miRNAs mentioned herein, the present invention also encompasses the use of variants and fragments thereof.

The term "variant" as used herein means an miRNA having a certain homology with the wild type miRNA sequence or the SEQ ID NOs disclosed herein. The term "homology" can be equated with "identity".

A variant miRNA sequence may include a nucleotide sequence which may be at least 50%, at least 55%, at least 65%, at least 70%, at least 75%, at least 80%, at least 85% or at least 90% identical, preferably at least 95%, at least 96%, at least 97%, at least 98%, or at least 99% identical to the subject miRNA sequence. Typically, the miRNA variants will have similar chemical properties/functions, e.g. effect the same gene regulation, as the subject miRNA sequence. Although homology can also be considered in terms of similarity (i.e. amino acid residues having similar chemical properties/functions), in the context of the present invention it is preferred to express homology in terms of sequence identity.

Identity comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each nucleotide in one sequence is directly compared with the corresponding nucleotide in the other sequence, one residue at a time. This is called an "ungapped" alignment. Typically, such ungapped alignments are performed only over a relatively short number of residues.

Although this is a very simple and consistent method, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical nucleotides, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) Nucleic Acids Res. 12:387). Examples of other software that can perform sequence comparisons include, but are not limited to, the BLAST package (see Ausubel et al. (1999) ibid-Ch. 18), FASTA (Atschul et al. (1990) J. Mol. Biol. 403-410) and the GENEWORKS suite of comparison tools. Both BLAST and FASTA are available for offline and online searching (see Ausubel et al. (1999) ibid, pages 7-58 to 7-60). However, for some applications, it is preferred to use the GCG Bestfit program. Another tool, called BLAST 2 Sequences is also available for comparing nucleotide sequences (see FEMS Microbiol. Lett. (1999) 174:247-50; FEMS Microbiol. Lett. (1999) 177:187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62. Suitably, the percentage identity is determined across the entirety of the reference and/or the query sequence.

Once the software has produced an optimal alignment, it is possible to calculate percentage homology, preferably percentage sequence identity. The software typically does this as part of the sequence comparison and generates a numerical result.

"Fragments" typically refers to a selected region of the miRNA that is of interest functionally. "Fragment" thus refers to a miRNA sequence that is a portion of a full-length miRNA.

Such variants and fragments may be prepared using standard techniques.

Regulation of Gene Expression

The inventors have shown that miR-3126 specifically modulates the expression of genes including those genes encoding Ninein, Unc-13 homolog D, Sulfatase 2, IL-32, OXER1, TMEM127, Butyrophilin, Integrin subunit alpha 2, Integrin beta 1, tubulin alpha 4A, tubulin beta 6, tubulin beta 2A and/or tubulin beta 2B.

Accordingly, in one aspect the present invention provides use of miR-3126 to modulate gene expression of one or more gene selected from: Ninein, Unc-13 homolog D, Sulfatase 2, IL-32, OXER1, TMEM127, Butyrophilin, Integrin subunit alpha 2, Integrin beta 1, tubulin alpha 4A, tubulin beta 6, tubulin beta 2A and tubulin beta 2B. and Butyrophilin.

Ninein

The inventors have shown that miR-3126 significantly increases expression of Ninein.

Accordingly, in one aspect the invention provides for use of miR-3126 to increase gene expression of Ninein.

Ninein (UniProt Q8N4C6) is also known as hNinein, glycogen synthase kinase 3 beta-interacting protein and GSK3B-interacting protein.

Ninein is a centrosomal protein required in the positioning and anchorage of the microtubule minus-end in epithelial cells. Ninein may also act as a centrosome maturation factor and may play a role in microtubule nucleation, by recruiting the gamma-tubulin ring complex to the centrosome. Ninein overexpression does not perturb nucleation or elongation of microtubules but suppresses release of microtubules. Ninein is required for centriole organization and microtubule anchoring at the mother centriole. Ninein may, therefore, have a role in growth and development.

Ninein may have a role in neuronal development. For instance, it has been shown that alternative splicing in Ninein appears to be sufficient to differentiate neural progenitor cells (NPCs) to neurons (Zhang, X., et al., 2016. Cell, 166(5), pp. 1147-1162).

Ninein may also have a role in epidermal development. In mammalian skin, Ninein localizes to the centrosomes of progenitor cells and relocates to the cell cortex upon differentiation of keratinocytes. It has been shown that Ninein is necessary for maintaining regular protein levels of the differentiation markers filaggrin and involucrin, for the formation of desmosomes, for the secretion of lamellar bodies, and for the formation of the epidermal barrier. Ninein-deficient mice are viable but develop a thinner skin with partly impaired epidermal barrier. (Lecland, N., et al., 2019. Life science alliance, 2(2), p.e201900373).

Unc-13 Homolog D

The inventors have shown that miR-3126 significantly increases expression of Unc-13 homolog D.

Accordingly, in one aspect the invention provides for use of miR-3126 to increase gene expression of Unc-13 homolog D.

Unc-13 homolog D (UniProt Q70J99) is also known as Munc13-4.

Unc-13 homolog D plays a role in cytotoxic granule exocytosis in lymphocytes. Unc-13 homolog D is required for both granule maturation and granule docking and priming at the immunologic synapse. Unc-13 homolog D regulates assembly of recycling and late endosomal structures, leading to the formation of an endosomal exocytic compartment that fuses with perforin-containing granules at the immunologic synapse and licences them for exocytosis. Unc-13 homolog D also regulates Ca2+-dependent secretory lysosome exocytosis in mast cells.

Unc-13 homolog D may have a role in protection against infection and a role in the leukocyte killing system. Mutations in the UNC13D gene are associated with haemophagocytic lymphohistiocytosis type 3. Haemophagocytic lymphohistiocytosis is an uncommon hematologic disorder seen more often in children than in adults. It is a life-threatening disease of severe hyperinflammation caused by uncontrolled proliferation of activated lymphocytes and macrophages, characterised by proliferation of morphologically benign lymphocytes and macrophages that secrete high amounts of inflammatory cytokines. It is classified as one of the cytokine storm syndromes.

Sulfatase 2

The inventors have shown that miR-3126 significantly increases expression of Sulfatase 2.

Accordingly, in one aspect the invention provides for use of miR-3126 to increase gene expression of Sulfatase 2.

Sulfatase 2 (UniProt Q8IWU5) is also known as extracellular sulfatase Sulf-2 and hSulf-2.

Sulfatase 2 exhibits arylsulfatase activity and highly specific endoglucosamine-6-sulfatase activity. Sulfatase 2 can remove sulfate from the C-6 position of glucosamine within specific subregions of intact heparin.

Sulfatase 2 may have a role in neuronal development. Sulfatase 2 modulates the cell fate change from motor neurons (MNs) to oligodendrocyte precursor cells (OPCs) by regulating Shh signaling in the mouse ventral spinal cord in coordination with Sulf1. (Jiang, W., et al., 2017. Developmental neuroscience, 39(5), pp. 361-374).

IL-32

The inventors have shown that miR-3126 significantly increases expression of IL-32.

Accordingly, in one aspect the invention provides for use of miR-3126 to increase gene expression of IL-32.

IL-32 (UniProt P24001) is also known as Interleukin-32, Natural killer cells protein 4, and Tumor necrosis factor alpha-inducing factor.

IL-32 is a cytokine that may play a role in innate and adaptive immune responses. IL-32 induces various cytokines such as TNFA/TNF-alpha and IL8. IL-32 activates typical cytokine signal pathways of NF-kappa-B and p38 MAPK.

IL-32 may have a role in protecting against allergies and/or an anti-inflammatory role. Abnormal presence of IL-32 has been repeatedly noticed during the pathogenesis of allergic, infectious, cancerous, and inflammatory diseases. Of particular note is the observation of the anti-inflammatory property of IL-32 in a murine ovalbumin model of allergic asthma. Compared to wild-type mice, IL-32γ transgenic mice show decreased levels of inflammatory cells, recruited eosinophils, and lymphocytes in bronchoalveolar lavage fluid in a mouse model of acute asthma. (Xin, T., et al., 2018. Respiratory research, 19(1), p. 124).

OXER1

The inventors have shown that miR-3126 significantly decreases expression of OXER1.

Accordingly, in one aspect the invention provides for use of miR-3126 to decrease gene expression of OXER1.

OXER1 (UniProt Q8TDS5) is also known as Oxoeicosanoid receptor 1, 5-oxo-ETE G-protein coupled receptor, G-protein coupled receptor 170, G-protein coupled receptor R527, and G-protein coupled receptor TG1019.

OXER1 is a receptor for eicosanoids and polyunsaturated fatty acids such as 5-oxo-6E,8Z,11Z,14Z-eicosatetraenoic acid (5-OXO-ETE), 5 (S)-hydroperoxy-6E,8Z,11Z, 14Z-eicosatetraenoic acid (5 (S)-HPETE) and arachidonic acid. OXER1 seems to be coupled to the G (i)/G (o), families of heteromeric G proteins.

OXER1 may have an anti-inflammatory role. Further, OXER1 may have a role in protecting against allergies. OXER1 is activated by 5-oxo-ETE, 5-HETE, and other members of the 5-Hydroxyicosatetraenoic acid family of arachidonic acid metabolites and thereby mediates this family's stimulatory effects on cell types that are involved in mediating immunity-based inflammatory reactions such as neutrophils, monocytes, and macrophages) as well as allergic reactions such as eosinophils and basophils. OXER1 also mediates the in vitro proliferation and other pro-malignant responses of cultured prostate, breast, ovary, and kidney cancer cells to the 5-HETE family of agonists. These studies suggest that OXER1 may be involved in orchestrating inflammatory and allergic responses in humans and contribute to the growth and spread of human prostate, breast, ovary, and kidney cancers. OXER1 is responsible for steroid production response to 5-oxo-ETE by human steroidogenic cells in vitro and therefore could be involved in steroid production in humans. It has been shown that feline leukocytes synthesize and respond to 5-oxo-ETE, which could potentially play an important role in feline asthma. (Cossette, C., et al., 2015. Biochemical pharmacology, 96(3), pp. 247-255.)

TMEM127

The inventors have shown that miR-3126 significantly decreases expression of TMEM127.

Accordingly, in one aspect the invention provides for use of miR-3126 to decrease gene expression of TMEM127.

TMEM127 (UniProt O75204) is also known as Transmembrane protein 127.

TMEM127 controls cell proliferation acting as a negative regulator of TOR signaling pathway mediated by mTORC1. TMEM127 may act as a tumor suppressor. Inactivating germline mutations cause hereditary pheochromocytoma and paraganglioma (Qin, Y., et al., 2010. Nature genetics, 42(3), p. 229; and Neumann, H. P., et al., 2011. The Journal of Clinical Endocrinology & Metabolism, 96(8), pp. E1279-E1282).

Butyrophilin

The inventors have shown that miR-3126 significantly increases expression of Butyrophilin.

Accordingly, in one aspect the invention provides for use of miR-3126 to increase gene expression of Butyrophilin.

Butyrophilin (UniProt Q13410) is also known as Butyrophilin subfamily 1 member A1 or BT.

Butyrophilin may function in the secretion of milk-fat droplets. Butyrophilin may act as a specific membrane-associated receptor for the association of cytoplasmic droplets with the apical plasma membrane. Butyrophilin may inhibit the proliferation of CD4 and CD8 T-cells activated by anti-CD3 antibodies, T-cell metabolism and IL2 and IFNG secretion.

Integrins [ITGA2 (Integrin Subunit Alpha 2), and ITGB1 (Integrin Subunit Beta 1)]

The inventors have shown that miR-3126 significantly increases expression of ITGA2 and ITGB1. Accordingly, in one aspect the invention provides for use of miR-3126 to increase gene expression of ITGA2 and/or ITGB1 genes.

ITGA2 (UniProt P17301) is also known as Integrin Subunit Alpha 2, Integrin, Alpha 2 and Platelet Membrane Glycoprotein Ia orr CD49b or VLA2.

ITGB1 (UniProt P05556) is also known as Integrin Subunit Beta 1, Integrin, Beta 1 and Glycoprotein IIa or CD29 or FNRB, MSK12, MDF2

Integrins have two main functions, attachment of the cells to the extracellular matrix (ECM) and signal transduction from the ECM to the cells thereby integrins have pleiotropic cell-specific roles including normal blood cloting, extravasation, cell-to-cell adhesion or cell migration. Growing evidence indicates that collagen-binding integrins and particularly alpha2/beta1 are important regulatory molecules of T-cell activation. It has been shown that alpha2/beta1 integrin costimulates the production of IFN-g signature cytokine in human effector T cells (also called Th1) suggesting important role in optimal immune response against pathogens (Mol Immunol. 2007 July; 44(15): 3732-40, www.ncbi.nlm.nih.gov/pubmed/17521731. Besides its role in co-stimulation, alpha2/beta1 integrin can also promote the migration, the localization and the retention of IFN-g producing Th1 cells in infected tissues for optimal pathogen clearance.

Tubulins [TUBA4A (Tubulin Alpha 4A), TUBB6 (Tubulin Beta 6 Class V), TUBB2A (Tubulin Beta 2a Class IIa), TUBB2B (Tubulin Beta 2b Class IIb)]

The inventors have shown that miR-3126 significantly increases expression of TUBA4A (Tubulin alpha 4A), TUBB6 (Tubulin beta 6 class V), TUBB2A (Tubulin beta 2a Class IIa) and TUBB2B (Tubulin beta 2b Class IIb).

Accordingly, in one aspect the invention provides for use of miR-3126 to increase gene expression of at least one gene selected in the group consisting of: TUBA4A, TUBA4A (Tubulin alpha 4A), TUBB6 (Tubulin beta 6 class V), TUBB2A (Tubulin beta 2a Class IIa) and TUBB2B (Tubulin beta 2b Class IIb)

In one embodiment, the invention provides for use of miR-3126 to increase gene expression of TUBA4A.

TUBA4A (UniProt P68366) is also known as Tubulin alpha 4A and Tubulin alpha 1 (TUBA1).

TUBA4A (Tubulin Alpha 4a) is a Protein Coding gene. Tubulin is the major constituent of microtubules. It binds two moles of GTP, one at an exchangeable site on the beta chain and one at a non-exchangeable site on the alpha chain. Microtubules of the eukaryotic cytoskeleton perform essential and diverse functions and are composed of a heterodimer of alpha and beta tubulin. The genes encoding these microtubule constituents are part of the tubulin superfamily, which is composed of six distinct families. Genes from the alpha, beta and gamma tubulin families are found in all eukaryotes. The alpha and beta tubulins represent the major components of microtubules, while gamma tubulin plays a critical role in the nucleation of microtubule assembly. There are multiple alpha and beta tubulin genes and they are highly conserved among and between species. TUBA4A encodes an alpha tubulin that is a highly conserved homolog of a rat testis-specific alpha tubulin. Alternatively spliced transcript variants encoding different isoforms have been found for this gene.

In another embodiment, the invention provides for use of miR-3126 to increase gene expression of TUBB6.

TUBB6 (UniProt Q9BUF5) is also known as Tubulin beta 6 and Tubulin Beta 6 Class V (TUBB6).

TUBB6 (Tubulin Beta 6 Class V) is a Protein Coding gene.

Tubulin is the major constituent of microtubules. It binds two moles of GTP, one at an exchangeable site on the beta chain and one at a non-exchangeable site on the alpha chain.

In another embodiment, the invention provides for use of miR-3126 to increase gene expression of TUBB2A.

TUBB2A (UniProt Q13885) is also known as Tubulin Beta 2A Class IIa, Class IIa Beta-Tubulin and Tubulin beta 2A.

TUBB2A (Tubulin Beta 2A Class IIa) is a Protein Coding gene.

Tubulin is the major constituent of microtubules. It binds two moles of GTP, one at an exchangeable site on the beta chain and one at a non-exchangeable site on the alpha chain.

In another embodiment, the invention provides for use of miR-3126 to increase gene expression of TUBB2B.

TUBB2B (UniProt Q9BVA1) is also known as Tubulin Beta 2B Class IIb, Class IIb Beta-Tubulin and Tubulin beta 2B.

TUBB2B (Tubulin Beta 2B Class IIb) is a Protein Coding gene.

Tubulin is the major constituent of microtubules. It binds two moles of GTP, one at an exchangeable site on the beta chain and one at a non-exchangeable site on the alpha chain.

Microtubules are essential for many aspects of polarity in multicellular organisms, ranging from the asymmetric distribution of cell-fate determinants in the one-cell embryo to the transient polarity generated in migrating fibroblasts. Epithelial cells exhibit permanent cell polarity characterized by apical and basolateral surface domains of distinct protein and lipid composition that are segregated by tight junctions. They are also endowed with a microtubule network that reflects the asymmetry of their cell surface: microtubule minus-ends face the apical- and microtubule plus-ends the basal domain. Strikingly, the formation of distinct surface domains during epithelial differentiation is accompanied by the re-organization of microtubules from a uniform array focused at the centrosome to the noncentrosomal network that aligns along the apico-basolateral polarity axis. The significance of this coincidence for epithelial morphogenesis and the signaling mechanisms that drive microtubule repolymerization in developing epithelia remain major unresolved questions that we are only beginning to address. Studies in cultured polarized epithelial cells have established that microtubules serve as tracks that facilitate targeted vesicular transport. Novel findings suggest, moreover, that microtubule-based transport promotes protein sorting, and even the generation of transport carriers in the endo- and exocytic pathways. (Musch, Traffic, January 2004, volume 5, Issue 1).

Globally it is well established that microtubules are required for efficient epithelial tight junction homeostasis, barrier maintenance and restoration upon challenges (Lila et al., *Am J Physiol Cell Physiol* 307: C245-C254, 2014). Indeed when microtubule dynamic is chemically altered, occluding trafficking, formation and maintenance of tight junctions are reduced with overall impact on transepithelial resistance.

Modulation of Biological Pathways

The inventors have shown that miR-3126 specifically activates certain pathways including Aryl Hydrocarbon Receptor Signaling pathway and/or Epithelial Adherens Junction signaling pathway.

Accordingly, in one aspect the present invention provides use of miR-3126 to activate one or more signalling pathways selected in the group consisting of: Aryl Hydrocarbon Receptor Signaling pathway and Epithelial Adherens Junction signaling pathway.

Aryl Hydrocarbon Receptor Signaling

Aryl Hydrocarbon Receptor (AHR) is a transcription factor that can bind xenobiotic chemicals. AHR has been shown to be involved in the regulation of cell physiology (migration, proliferation and adhesion) (Larigot et al., 2018, AhR signaling pathways and regulatory functions. Biochim Open 7, 1-9).

AHR is also important for development of the nervous system (Kimura and Tohyama, 2017, Embryonic and Postnatal Expression of Aryl Hydrocarbon Receptor mRNA in Mouse Brain Front Neuroanat 11, 4). It has been reported that in utero disruption of AHR signaling leads to abnormal neuronal dendritic growth in mice (Kimura et al., 2015, Developmental origin of abnormal dendritic growth in the mouse brain induced by in utero disruption of aryl hydrocarbon receptor signaling. Neurotoxicol Teratol 52, 42-50).

In addition, AHR has been shown to play a role in the maintenance of the intestinal barrier (Esser and Rannug, 2015, The aryl hydrocarbon receptor in barrier organ physiology, immunology, and toxicology. Pharmacol Rev 67, 259-279) and to regulate immune surveillance within the intestine (Murray et al., 2016, "Expression of the aryl hydrocarbon receptor contributes to the establishment of intestinal microbial community structure in mice". Sci Rep 6, 33969; Qiu et al., 2012, "The aryl hydrocarbon receptor regulates gut immunity through modulation of innate lymphoid cells". Immunity 36, 92-104). Moreover, it has been shown that AHR in mice contributes to the establishment of the gut microbiota (Murray et al., 2016). Interestingly, AHR ligands such as Polyphenols (Larigot et al., 2018) have antioxidant, anti-inflammatory, neuroprotective, anti-diabetic, and anti-adipogenic properties. Taken together, these findings strongly suggest that AHR signalling modulation by miRNAs could be beneficial in the promotion of intestinal cell development and function and likely by microbiota composition modulation, immune surveillance within the intestine and or gut barrier maintenance/formation.

miR-3126 activates Aryl Hydrocarbon Receptor Signaling and accordingly it may be beneficial in the promotion of nervous system growth, in the promotion of Microbiota establishment and/or in the promotion of intestinal barrier integrity and/or function and of associated protection of the subject.

Epithelial Adherens Junction Signaling.

Adherens junction proteins such as Cadherins are responsible for intercellular adhesion as well as for maintaining cell polarity and regulating epithelial migration and proliferation (Groschwitz and Hogan, 2009, Intestinal barrier function: molecular regulation and disease pathogenesis. J Allergy Clin Immunol 124, 3-20; quiz 21-22). Adherens junction and tight junction have been shown to ensure the gut barrier function due to their ability to maintain cell-to-cell connection. After birth, intestinal barrier of newborn babies is more permeable than that of adults and barrier function progressively increases during early life, a process that could be modulated by miR-3126-5p.

miR-3126 activates Aryl Hydrocarbon Receptor Signaling and accordingly it may be beneficial in the promotion of gut barrier maintenance and associated protection of the subject.

Uses of miR-3126 and the Nutritional Composition

In one aspect the invention provides miR-3126 for use as a medicament. In a related aspect the invention provides for use of miR-3126 for the manufacture of a medicament. In a related aspect the invention provides a method of treatment comprising administering miR-3126.

In another aspect the invention provides the nutritional composition of the invention for use as a medicament. In a related aspect the invention provides for use of the nutritional composition of the invention for the manufacture of a medicament. In a related aspect the invention provides a method of treatment comprising administering the nutritional composition of the invention.

Gastrointestinal Health

As well as the effects on gene expression described above, the present inventors have performed a biological function analysis. Inferred biological functions of miR-3126 include: (i) upregulation of migration of cells, the differentiation of epithelial cells and neovascularisation; and (ii) downregulation of survival of tumour cell lines, infections and gastrointestinal tumours. Based on these results and the effects on gene expression, miR-3126 may promote and/or protect gastrointestinal health.

In one aspect the invention provides miR-3126 for use in promoting and/or protecting gastrointestinal health. In a related aspect the invention provides for use of miR-3126 for the manufacture of a medicament for promoting and/or protecting gastrointestinal health. In a related aspect the invention provides a method of promoting and/or protecting gastrointestinal health of a subject, comprising administering miR-3126 to the subject.

In one aspect the invention provides the nutritional composition of the invention for use in promoting and/or protecting gastrointestinal health. In a related aspect the invention provides the nutritional composition of the invention for the manufacture of a medicament for promoting and/or protecting gastrointestinal health. In a related aspect the invention provides a method of promoting and/or protecting gastrointestinal health of a subject, comprising administering the nutritional composition of the invention to the subject.

In one aspect the invention provides use of miR-3126 in promoting and/or protecting gastrointestinal health. In another aspect the invention provides use of the nutritional composition of the invention in promoting and/or protecting gastrointestinal health.

Growth and Development

As described above, the inventors have shown that miR-3126 significantly decreases expression of TMEM127, which has a role in role in cell proliferation (growth).

In one aspect the invention provides miR-3126 for use in promoting growth and/or development. In a related aspect the invention provides for use of miR-3126 for the manufacture of a medicament for promoting growth and/or development. In a related aspect the invention provides a method of promoting growth and/or development of a subject comprising administering miR-3126 to the subject.

In one aspect the invention provides the nutritional composition of the invention for use in promoting growth and/or development. In a related aspect the invention provides the nutritional composition of the invention for the manufacture of a medicament for promoting growth and/or development. In a related aspect the invention provides a method of promoting growth and/or development of a subject comprising administering the nutritional composition of the invention to the subject.

In one aspect the invention provides use of miR-3126 in promoting growth and/or development. In another aspect the invention provides use of the nutritional composition of the invention in promoting growth and/or development.

Neuronal Development

As described above, the inventors have shown that miR-3126 significantly increases expression of Ninein and Sulfatase 2, which may both have a role in neuronal development.

Additionally, miR-3126 activates the Aryl Hydrocarbon receptor signalling pathway which also promotes nervous system growth.

Defects in neural development can lead to malformations and a wide variety of neurodevelopmental disorders. Children with neurodevelopmental disorders can experience difficulties with language and speech, motor skills, behaviour, memory, learning, or other neurological functions.

In one aspect the invention provides miR-3126 for use in promoting central nervous system (CNS) development. In a related aspect the invention provides for use of miR-3126 for the manufacture of a medicament for promoting CNS development. In a related aspect the invention provides a method of promoting CNS development of a subject comprising administering miR-3126 to the subject.

In one aspect the invention provides the nutritional composition of the invention for use in promoting CNS development. In a related aspect the invention provides the nutritional composition of the invention for the manufacture of a medicament for promoting CNS development. In a related aspect the invention provides a method of promoting CNS development of a subject comprising administering the nutritional composition of the invention to the subject.

In one aspect the invention provides use of miR-3126 in promoting CNS development. In another aspect the invention provides use of the nutritional composition of the invention in promoting CNS development.

Epidermal Development

As described above, the inventors have shown that miR-3126 significantly increases expression of Ninein, which may have a role in epidermal development.

Defects in epidermal development can lead to tissue fragility, skin hypertrophic and inflammatory conditions or malignant transformation of epidermal keratinocyte.

In one aspect the invention provides miR-3126 for use in promoting epidermal development. In a related aspect the invention provides for use of miR-3126 for the manufacture of a medicament for promoting epidermal development. In a related aspect the invention provides a method of promoting epidermal development of a subject comprising administering miR-3126 to the subject.

In one aspect the invention provides the nutritional composition of the invention for use in promoting epidermal development. In a related aspect the invention provides the nutritional composition of the invention for the manufacture of a medicament for promoting epidermal development. In a related aspect the invention provides a method of promoting epidermal development of a subject comprising administering the nutritional composition of the invention to the subject.

In one aspect the invention provides use of miR-3126 in promoting epidermal development. In another aspect the invention provides use of the nutritional composition of the invention in promoting epidermal development.

Infection

As described above, the inventors have shown that miR-3126 significantly increases expression of Unc-13 homolog D and several integrins as above mentioned which may have a role in protection against infection.

In one aspect the invention provides miR-3126 for use in reducing the risk of infection. In a related aspect the invention provides for use of miR-3126 for the manufacture of a medicament for reducing the risk of infection. In a related aspect the invention provides a method of reducing the risk of infection in a subject comprising administering miR-3126 to the subject.

In one aspect the invention provides miR-3126 for use in preventing and/or treating an infection. In a related aspect the invention provides for use of miR-3126 for the manufacture of a medicament for preventing and/or treating an infection. In a related aspect the invention provides a method of preventing and/or treating an infection in a subject comprising administering miR-3126 to the subject.

In one aspect the invention provides the nutritional composition of the invention for use in reducing the risk of infection. In a related aspect the invention provides the nutritional composition of the invention for the manufacture of a medicament for reducing the risk of infection. In a related aspect the invention provides a method of reducing the risk of infection in a subject comprising administering the nutritional composition of the invention to the subject.

In one aspect the invention provides the nutritional composition of the invention for use in preventing and/or treating an infection. In a related aspect the invention provides the nutritional composition of the invention for the manufacture of a medicament for preventing and/or treating an infection. In a related aspect the invention provides a method of preventing and/or treating an infection in a subject comprising administering the nutritional composition of the invention to the subject.

In one aspect the invention provides use of miR-3126 in reducing the risk of infection. In another aspect the invention provides use of the nutritional composition of the invention in reducing the risk of infection.

In one aspect the invention provides use of miR-3126 in preventing and/or treating an infection. In another aspect the invention provides use of the nutritional composition of the invention in preventing and/or treating an infection.

Lymphoproliferative Disorders

As described above, the inventors have shown that miR-3126 significantly increases expression of Unc-13 homolog D, which may have a role in the leukocyte killing system and protection against lymphoproliferative disorders.

Lymphoproliferative disorders (LPDs) refer to several conditions in which lymphocytes are produced in excessive quantities. They typically occur in people who have a compromised immune system.

In one aspect the invention provides miR-3126 for use in reducing the risk of a subject developing a lymphoproliferative disorder. In a related aspect the invention provides for use of miR-3126 for the manufacture of a medicament for reducing the risk of a subject developing a lymphoproliferative disorder. In a related aspect the invention provides a method of reducing the risk of a subject developing a lymphoproliferative disorder, comprising administering miR-3126 to the subject.

In one aspect the invention provides miR-3126 for use in preventing and/or treating a lymphoproliferative disorder. In a related aspect the invention provides for use of miR-3126 for the manufacture of a medicament for preventing and/or treating a lymphoproliferative disorder. In a related aspect the invention provides a method of preventing and/or treating a lymphoproliferative disorder in a subject, comprising administering miR-3126 to the subject.

In one aspect the invention provides the nutritional composition of the invention for use in reducing the risk of a subject developing a lymphoproliferative disorder. In a related aspect the invention provides the nutritional composition of the invention for the manufacture of a medicament for reducing the risk of a subject developing a lymphoproliferative disorder. In a related aspect the invention provides a method of reducing the risk of a subject developing a lymphoproliferative disorder, comprising administering the nutritional composition of the invention to the subject.

In one aspect the invention provides the nutritional composition of the invention for use in preventing and/or treating a lymphoproliferative disorder. In a related aspect the invention provides the nutritional composition of the invention for the manufacture of a medicament for preventing and/or treating a lymphoproliferative disorder. In a related aspect the invention provides a method of preventing and/or treating a lymphoproliferative disorder in a subject, comprising administering the nutritional composition of the invention to the subject.

In one aspect the invention provides use of miR-3126 in reducing the risk of a subject developing a lymphoproliferative disorder. In another aspect the invention provides use of the nutritional composition of the invention in reducing the risk of a subject developing a lymphoproliferative disorder.

In one aspect the invention provides use of miR-3126 in preventing and/or treating a lymphoproliferative disorder. In another aspect the invention provides use of the nutritional composition of the invention in preventing and/or treating a lymphoproliferative disorder.

Allergy

As described above, the inventors have shown that miR-3126 significantly increases expression of IL-32 and significantly decreases expression of OXER1. Both IL-32 and OXER 1 may have a role in protecting against allergic diseases.

Allergic diseases are a number of conditions caused by hypersensitivity of the immune system to typically harmless substances in the environment. Allergic diseases include hay fever, food allergies, atopic dermatitis, allergic asthma, and anaphylaxis. In one embodiment the allergic disease is allergic asthma.

In one aspect the invention provides miR-3126 for use in reducing the risk of a subject developing an allergic disease. In a related aspect the invention provides for use of miR-3126 for the manufacture of a medicament for reducing the risk of a subject developing an allergic disease. In a related aspect the invention provides a method of reducing the risk of a subject developing an allergic disease, comprising administering miR-3126 to the subject.

In one aspect the invention provides miR-3126 for use in preventing and/or treating an allergic disease. In a related aspect the invention provides for use of miR-3126 for the manufacture of a medicament for preventing and/or treating an allergic disease. In a related aspect the invention provides a method of preventing and/or treating an allergic disease in a subject, comprising administering miR-3126 to the subject.

In one aspect the invention provides the nutritional composition of the invention for use in reducing the risk of a subject developing an allergic disease. In a related aspect the invention provides the nutritional composition of the invention for the manufacture of a medicament for reducing the risk of a subject developing an allergic disease. In a related aspect the invention provides a method of reducing the risk of a subject developing an allergic disease, comprising administering the nutritional composition of the invention to the subject.

In one aspect the invention provides the nutritional composition of the invention for use in preventing and/or treating an allergic disease. In a related aspect the invention provides the nutritional composition of the invention for the manufacture of a medicament for preventing and/or treating an allergic disease. In a related aspect the invention provides a method of preventing and/or treating an allergic disease in a subject, comprising administering the nutritional composition of the invention to the subject.

In one aspect the invention provides use of miR-3126 in reducing the risk of a subject developing an allergic disease. In another aspect the invention provides use of the nutritional composition of the invention in reducing the risk of a subject developing an allergic disease.

In one aspect the invention provides use of miR-3126 in preventing and/or treating an allergic disease. In another aspect the invention provides use of the nutritional composition of the invention in preventing and/or treating an allergic disease.

Inflammation

As described above, the inventors have shown that miR-3126 significantly increases expression of IL-32 and significantly decreases expression of OXER1. Both IL-32 and OXER 1 may have an anti-inflammatory role.

In one aspect the invention provides miR-3126 for use in reducing the risk of a subject developing an inflammatory disorder. In a related aspect the invention provides for use of miR-3126 for the manufacture of a medicament for reducing the risk of a subject developing an inflammatory disorder. In a related aspect the invention provides a method of reducing the risk of a subject developing an inflammatory disorder, comprising administering miR-3126 to the subject.

In one aspect the invention provides miR-3126 for use in preventing and/or treating an inflammatory disorder. In a related aspect the invention provides for use of miR-3126 for the manufacture of a medicament for preventing and/or treating an inflammatory disorder. In a related aspect the invention provides a method of preventing and/or treating an inflammatory disorder in a subject, comprising administering miR-3126 to the subject.

In one aspect the invention provides the nutritional composition of the invention for use in reducing the risk of a subject developing an inflammatory disorder. In a related aspect the invention provides the nutritional composition of the invention for the manufacture of a medicament for reducing the risk of a subject developing an inflammatory disorder. In a related aspect the invention provides a method of reducing the risk of a subject developing an inflammatory disorder, comprising administering the nutritional composition of the invention to the subject.

In one aspect the invention provides the nutritional composition of the invention for use in preventing and/or treating an inflammatory disorder. In a related aspect the invention provides the nutritional composition of the invention for the manufacture of a medicament for preventing and/or treating an inflammatory disorder. In a related aspect the invention provides a method of preventing and/or treating an inflammatory disorder in a subject, comprising administering the nutritional composition of the invention to the subject.

In one aspect the invention provides use of miR-3126 in reducing the risk of a subject developing an inflammatory disorder. In another aspect the invention provides use of the nutritional composition of the invention in reducing the risk of a subject developing an inflammatory disorder.

In one aspect the invention provides use of miR-3126 in preventing and/or treating an inflammatory disorder. In another aspect the invention provides use of the nutritional composition of the invention in preventing and/or treating an inflammatory disorder.

Gut Barrier

As described above, the inventors have shown that miR-3126 significantly increases expression of several tubulins and also activates the Aryl Hydrocarbon receptor Signaling, and Epithelial Adherens Junction signalling pathways.

Such genes' expression and pathway activation as above discussed has a role in the promoting of gut barrier development and function (including gut barrier integrity and manteinance). Disruption of the gut barrier has been associated with many gastrointestinal diseases, but also with extra-intestinal pathological condition, such as type 1 diabetes mellitus, allergic diseases or autism spectrum disorders. The maintenance of a healthy intestinal barrier is therefore of paramount importance in children" (Viggiano et al. Eur Rev Med Pharmacol Sci. 2015; 19(6): 1077-85).

Defects in gut barrier development and function can lead to a wide variety of disorders, for example: celiac disease, infectious diarrhea, inflammatory bowel disease, sepsis, NEC or post-infectious IBS.

In one aspect the invention provides miR-3126 for use in promoting gut barrier integrity and function. In a related aspect the invention provides for use of miR-3126 for the manufacture of a medicament for promoting gut barrier development and function. In a related aspect the invention provides a method of promoting gut barrier development and function in a subject comprising administering miR-3126 to the subject.

In one aspect the invention provides the nutritional composition of the invention for use in promoting gut barrier development and function. In a related aspect the invention provides the nutritional composition of the invention for the manufacture of a medicament for promoting gut barrier development and funstion. In a related aspect the invention provides a method of promoting gut barrier development and function in subject comprising administering the nutritional composition of the invention to the subject.

In one aspect the invention provides use of miR-3126 in promoting gut barrier development and function. In another aspect the invention provides use of the nutritional composition of the invention in promoting gut barrier development and fuction.

The Subject miR-3126 and/or the nutritional composition of the invention may be administered to any subject in need thereof.

Preferably the subject is an infant or a young child. More preferably the subject is an infant. Thus, miR-3126 and/or the nutritional composition of the invention may be administered to an infant.

"Infant" means a child under the age of 12 months. Thus, miR-3126 and/or the nutritional composition of the invention may be administered to an infant, wherein the infant is 0-12 months of age. In one embodiment, the infant is 0-6 months of age.

In one embodiment the infant is 2-12 months of age, preferably 2-6 months of age.

In one embodiment the infant is 3-12 months of age, preferably 3-6 months of age.

Accordingly, in some embodiments miR-3126 and/or the nutritional composition of the invention are administered to an infant, wherein the infant is 3-6 months of age.

In some embodiments the infant or young child is a preterm infant or young child. A "preterm" or "premature" means an infant or young child who was not born at term. Generally it refers to an infant or young child born prior 36 weeks of gestation.

In some embodiments the infant or young child was born by C-section or was vaginally delivered.

Methods of Manufacture

The nutritional composition of the present invention may be prepared by any suitable method known in the art.

For example, a nutritional composition may be prepared by blending together a protein source, a carbohydrate source and a fat source in appropriate proportions. If used, emulsifiers may be included at this point. Vitamins and minerals may be added at this point but they may be added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The miRNA may be added at this point, especially if the final product is to have a liquid form. If the final product is to be a powder, they may likewise be added at this stage if desired. Alternatively the miRNA may be added later to avoid thermal degradation.

The liquid mixture may then be homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The miRNA may also or alternatively be added at this stage by dry-mixing or by blending and the mixture is spray-dried or freeze-dried.

If a liquid composition is preferred, the homogenised mixture may be sterilised then aseptically filled into suitable containers or may be first filled into the containers and then retorted.

EXAMPLES

Example 1—Longitudinal Profile and Analysis of miRNAs in Human Breast Milk Sample Processing Milk samples were collected from 44 individuals at three time points: V2, corresponding to about two weeks postpartum; V4, corresponding to about 2 months postpartum; and V5, corresponding to about 3 months postpartum.

Whole milk samples were first thawed on ice. miRNA profiling was performed with the HTG EdgeSeq platform, using the HTG EdgeSeq miRNA Whole Transcriptome Assay (HTG Molecular Diagnostics).

30 μL of whole milk was added to 30 μL of Plasma Lysis Buffer (ratio 1:1) complemented by 6 μL of Proteinase K (1/10). After a 3-hour incubation at 50° C. at 600 rpm, 26 μL of the mixture were transferred to the HTG platform for miRNA capture. miRNA-target specific probes hybridized against their corresponding miRNAs and protected them from S1 nuclease digestion. Base hydrolysis eliminated the captured miRNAs and the probes were conserved for indexing and sequencing library preparation.

Once the capture was completed, each sample was tagged with sequencing indexes and specific sample barcodes by a PCR step. The PCR mixture consisted of 15 μL OneTaq® Hot Start 2× Master Mix GC Buffer (NEB), 3 μL of each HTG tag primers (forward and reverse), 3 μL of the sample capture, and 6 μL of nuclease free water. Following a denaturation step of 4 min at 95° C., 20 PCR cycles were performed, consisting of a denaturation step of 15 s at 95° C., an annealing step of 45 s at 56° C. and an extension step of 45 s at 68° C. The PCR reaction was completed by a final step of 10 min at 68° C. PCR products were purified with CleanNGS beads (ratio 1:8) on SciClone NGS WorkStation (Perkin Elmer), and visualized on a LabChip GX High Sensitivity (Perkin Elmer) for the determination of their nucleic acids concentrations.

Purified PCR products were pooled by 24 samples on a liquid handling robotic platform at an equimolar concentration of 2 nM in 100 μL final volume. Pools were purified a second time with CleanNGS beads (ratio 1:8) and quantified with Qubit to precisely adjust the final concentration to 2 nM. The Illumina MiSeq sequencer was loaded with 20 μM of library spiked with 5% (v/v) PhiX. A MiSeq 150V3 kit was used for the sequencing of each pool.

Sequencing raw data (named "reads") were parsed using the HTG Processor software (version 2), and the mapped miRNA reads were further analyzed.

Data Analysis 6 samples set outside the 95% confidence interval ellipse and were therefore considered as outliers. As a consequence, these samples were excluded from the analysis dataset.

miRNAs which were below detection threshold in more than 50 samples were excluded. An offset value of 1 to the expression level was set prior to the log 2 transformation. From the Count per Million (CPM) distribution, we estimated the detection threshold to 7 CPMs. In total, 685 miRNAs were measured.

Three analytical approaches were used to analyse the dataset. To optimize the selection of miRNA expression profiles and decrease the number of false positive results, the intersection between the three analytical approaches were kept as the best miRNA profiles. These three approaches are described below.

Longitudinal Model with Quantile Normalization

In the first approach, the dataset was normalized using the quantile method.

The dataset was modelled with a linear mixed model. In order to correct as well for inter-donor variability during both time points, and at baseline, a random term for the donor was added to the model. To correct for gender profile discrepancies observed for some miRNA during both time points and at baseline, a gender random effect was added to the model. To correct for the sequencing run effect, a sequencing run random effect was added to the model. Eventually because we were performing more than 600 tests, we needed to correct for multiple testing. A typical 5% false discovery rate threshold was then applied to the results.

$$miRNA_{Expr} = \text{Time} + (\text{Donor}) + (\text{Gender}) + (SeqRun) + \text{Error}$$

Longitudinal Model with TMM Normalization

In the second approach, the dataset was normalized using the TMM method. The dataset was next modelled and tested with the same model as for the first approach.

Classical Differential Expression Between V5 and V2

In the third approach, the dataset was normalized using the quantile method but modelled with a simpler generalized linear model. This method does not account for the longitudinal design of the study and the non-independency of the samples belonging to the same donor.

$$miRNA_{Expr} = \text{Time} + SeqRun + \text{Error}$$

A typical 5% false discovery threshold was then applied to the results.

Results

Eleven dynamic miRNAs were identified with either an increasing or a decreasing expression during lactation. These are shown in Tables 2 and 3 below.

Thirty-eight miRNAs were identified which were highly and stably expressed during lactation. These are shown in Table 4 below.

TABLE 2 seven miRNA with increased expression during lactation

| miRNA human ID | miRNA human sequence |
|---|---|
| has-let-7d-3p | CUAUACGACCUGCUGCCUUUCU (SEQ ID NO: 43) |
| has-miR-196a-5p | UAGGUAGUUUCAUGUUGUUGGG (SEQ ID NO: 44) |
| has-miR-187-5p | GGCUACAACACAGGACCCGGGC (SEQ ID NO: 45) |
| has-miR-516a-5p | UUCUCGAGGAAAGAAGCACUUUC (SEQ ID NO: 46) |
| has-miR-92b-5p | AGGGACGGGACGCGGUGCAGUG (SEQ ID NO: 47) |
| has-miR-3126-5p | UGAGGGACAGAUGCCAGAAGCA (SEQ ID NO: 2) |
| has-miR-3184-3p | AAAGUCUCGCUCUCUGCCCCUCA (SEQ ID NO: 48) |

TABLE 3

| four miRNA with decreased expression during lactation | |
|---|---|
| miRNA human ID | miRNA human sequence |
| has-miR-34a-5p | UGGCAGUGUCUUAGCUGGUUGU (SEQ ID NO: 91) |
| has-miR-125b-5p | UCCCUGAGACCCUAACUUGUGA (SEQ ID NO: 22) |
| has-miR-146a-5p | UGAGAACUGAAUUCCAUGGGUU (SEQ ID NO: 92) |
| has-miR-1307-3p | ACUCGGCGUGGCGUCGGUCGUG (SEQ ID NO: 93) |

TABLE 4

| thirty-eight highly and stably expressed miRNA | |
|---|---|
| miRNA human ID | miRNA human sequence |
| has-let-7b-5p | UGAGGUAGUAGGUUGUGUGGUU (SEQ ID NO: 4) |
| has-let-7c-5p | UGAGGUAGUAGGUUGUAUGGUU (SEQ ID NO: 5) |
| has-miR-19b-3p | UGUGCAAAUCCAUGCAAAACUGA (SEQ ID NO: 6) |
| has-miR-22-3p | AAGCUGCCAGUUGAAGAACUGU (SEQ ID NO: 7) |
| has-miR-24-3p | UGGCUCAGUUCAGCAGGAACAG (SEQ ID NO: 8) |
| has-miR-25-3p | CAUUGCACUUGUCUCGGUCUGA (SEQ ID NO: 9) |
| has-miR-29a-3p | UAGCACCAUCUGAAAUCGGUUA (SEQ ID NO: 10) |
| has-miR-30a-5p | UGUAAACAUCCUCGACUGGAAG (SEQ ID NO: 11) |
| has-miR-92a-3p | UAUUGCACUUGUCCCGGCCUGU (SEQ ID NO: 12) |
| has-miR-99a-5p | AACCCGUAGAUCCGAUCUUGUG (SEQ ID NO: 13) |
| has-miR-100-5p | AACCCGUAGAUCCGAACUUGUG (SEQ ID NO: 14) |
| has-miR-197-3p | UUCACCACCUUCUCCACCCAGC (SEQ ID NO: 15) |
| has-miR-30d-5p | UGUAAACAUCCCCGACUGGAAG (SEQ ID NO: 16) |
| has-miR-181a-5p | AACAUUCAACGCUGUCGGUGAGU (SEQ ID NO: 17) |
| has-miR-181b-5p | AACAUUCAUUGCUGUCGGUGGGU (SEQ ID NO: 18) |
| has-miR-205-5p | UCCUUCAUUCCACCGGAGUCUG (SEQ ID NO: 19) |
| has-miR-210-3p | CUGUGCGUGUGACAGCGGCUGA (SEQ ID NO: 20) |
| has-miR-221-3p | AGCUACAUUGUCUGCUGGGUUUC (SEQ ID NO: 21) |

TABLE 4-continued

| thirty-eight highly and stably expressed miRNA | |
|---|---|
| miRNA human ID | miRNA human sequence |
| has-miR-125b-5p | UCCCUGAGACCCUAACUUGUGA (SEQ ID NO: 22) |
| has-miR-125a-5p | UCCCUGAGACCCUUUAACCUGUGA (SEQ ID NO: 23) |
| has-miR-149-3p | AGGGAGGGACGGGGGCUGUGC (SEQ ID NO: 24) |
| has-miR-193a-5p | UGGGUCUUUGCGGGCGAGAUGA (SEQ ID NO: 25) |
| has-miR-193a-3p | AACUGGCCUACAAAGUCCCAGU (SEQ ID NO: 26) |
| has-miR-320a | AAAAGCUGGGUUGAGAGGGCGA (SEQ ID NO: 27) |
| has-miR-200a-3p | UAACACUGUCUGGUAACGAUGU (SEQ ID NO: 28) |
| has-miR-99b-5p | CACCCGUAGAACCGACCUUGCG (SEQ ID NO: 29) |
| has-miR-130b-3p | CAGUGCAAUGAUGAAAGGGCAU (SEQ ID NO: 30) |
| has-miR-30e-5p | UGUAAACAUCCUUGACUGGAAG (SEQ ID NO: 31) |
| has-miR-375 | UUUGUUCGUUCGGCUCGCGUGA (SEQ ID NO: 32) |
| has-miR-378a-3p | ACUGGACUUGGAGUCAGAAGGC (SEQ ID NO: 33) |
| has-miR-151a-3p | CUAGACUGAAGCUCCUUGAGG (SEQ ID NO: 34) |
| has-miR-425-5p | AAUGACACGAUCACUCCCGUUGA (SEQ ID NO: 35) |
| has-miR-484 | UCAGGCUCAGUCCCCUCCCGAU (SEQ ID NO: 36) |
| has-miR-146b-5p | UGAGAACUGAAUUCCAUAGGCU (SEQ ID NO: 37) |
| has-miR-574-5p | UGAGUGUGUGUGUGUGAGUGUGU (SEQ ID NO: 38) |
| has-miR-652-3p | AAUGGCGCCACUAGGGUUGUG (SEQ ID NO: 39) |
| has-miR-320c | AAAAGCUGGGUUGAGAGGGU (SEQ ID NO: 40) |
| has-miR-3141 | GAGGGCGGGUGGAGGAGGA (SEQ ID NO: 41) |

Example 2—In Vitro Evaluation of miR-3184, miR-3126, and miR-3141

Sample Processing

Cell Culture and Transfection

Caco2 were cultured in DMEM (+) L-glutamate (−) Pyruvate supplemented with 1× non-essential amino acids, 1 mM Sodium Pyruvate and 20% FBS. Cells were split three times a week without exciding 80% confluency. For transfection, cells were plated in 24 well plate (50,000 cells/well) to obtain a 50% confluency the day after. Transfection was performed using DharmaFect 4 reagent from Dharmacon (cat #T-2004-01) following manufacturer recommendation. Briefly, 1.25 µl/well of DharmaFect 4 and a final concentration of 25 nM of miRNA were used. For each time point (i.e. 48 h and 72 h post transfection) media was removed and cells were washed with 1 ml of cold PBS without calcium chloride and magnesium chloride. Cells were frozen directly on plate after aspirating cold PBS.

miRNA were purchased from Dharmacon (Horizon Discovery), see table below.

| cat # | Name |
|---|---|
| C-301683-00-0020 | miRIDIAN microRNA Human hsa-miR-3141 - Mimic |
| C-301661-00-0020 | miRIDIAN microRNA Human hsa-miR-3126-5p - Mimic |
| C-302745-00-0020 | miRIDIAN microRNA Human hsa-miR-3184-3p - Mimic |
| C-301151-01-0020 | miRIDIAN microRNA Human hsa-miR-149-3p - Mimic |
| C-301113-01-0020 | miRIDIAN microRNA Human hsa-miR-574-5p - Mimic |
| CN-002000-01-20 | miRIDIAN microRNA Mimic Negative Control #2 |
| CP-004000-01-20 | Mimic Endogenous Positive Control (miR-122) |

RNA Extraction

RNA were extracted using the QIAymphony (from QIAGEN) robot and the RNA kit extraction (QIAGEN cat #931636) with the miRNA CT400 protocol. Cells were lyzed into 420 µl of RLT plus buffer and RNA was eluted into 100 µl. RNA quality and quantity were assessed using the Fragment Analyzer and the RiboGreen technology respectively.

QuantSeq Experiment and Sequencing

A starting material of 50 ng (RNA) was used for the QuantSeq protocol following manufacturer recommendations (cat #: 015.384 Lexogen). Libraries were sequenced single-end for 65 bp (SR50) on an Illumina HiSeq 2500 instrument using a High output SBS V4 kit. Samples were sequenced to a depth of 6-10 million reads.

Data Analysis

Gene expression levels were filtered prior to normalization and differential expression analysis. Genes with count per million of reads (CPM) below 19.89 in at least 9 samples were discarded. These genes were considered lowly expressed and below the level of detection. The gene expression levels for the remaining genes were then normalized. The normalization was done with the weighted trimmed means of the log expression ratios (TMM) method as described in Robinson, and Oshlack, Genome Biology 11, 2010. In order to estimate the differentially expressed genes, samples were grouped by treatment and time, and expression values were modeled with a quasi-likelihood negative binomial generalized log-linear model to count data as described in Lund, and Nettleton, Statistical Applications in Genetics and Molecular Biology. 2012. Model parameters were set as below:

$$Expgene = \text{group} + \text{batch}$$

Eventually multiple testing procedure and significance level cutoff to the genewise tests was performed to prevent false positive rate inflation due to the multiplication of the statistical tests performed.

Biological Function and Pathway Analysis with Ingenuity Pathway Analysis (IPA) Software Functional enrichment analysis was performed using Ingenuity Pathway Analysis (IPA) software. The analysis examines genes in the dataset that are known to affect functions, or pathways, compares the genes' direction of change to expectations derived from the literature, then issues a prediction for each function or pathway based on the direction of change. The direction of change is the gene expression in the experimental samples relative to a control. If the direction of change is consistent with the literature across most genes, IPA predicts that the function or pathway will increase in the experimental sample. If it is mostly inconsistent with the literature, IPA predicts that the function or pathway will decrease. If there is no clear pattern related to the literature, IPA does not make any prediction IPA uses the z-score algorithm to make predictions. The z-score algorithm is designed to reduce the chance that random data will generate significant predictions. See Krämer A. et al., Bioinformatics, 2014 for a detailed description of the algorithm.

Results

An in vitro Caco2 cell model was used to evaluate the effect of miR-3184-3p, miR-3126-5p, and miR-3141 on gene expression.

miR-3184-3p, miR-3126-5p, and miR-3141 significantly effected the expression of the genes shown in Table 5 below.

TABLE 5 in vitro evaluation of miR-3184, miR-3126, and miR-3141

| miRNA human ID | Gene expression log fold change miR treated cells versus control cells |
|---|---|
| miR-3184-3p | Lipin 2 + 1.54 |
| | IGF2 + 1.72 |
| miR-3126-5p | Ninein + 1.93 |
| | Unc-13 homolog D + 2.46 |
| | Sulfatase 2 + 2.29 |
| | IL-32 + 1.69 |
| | OXER1 −2.16 |
| | TMEM127 −3.14 |
| | Butyrophilin + 2.24 |
| | ITGA2 + 2.57 |
| | ITGB1 + 1.28 |
| | TUBA4A + 2.43 |
| | TUBB6 + 0.91 |
| | TUBB2A + 2.17 |
| | TUBB2B + 2.31 |
| miR-3141 | Claudin-2 + 4.35 |
| | SLC2A1 + 1.65 |

Modulation of pathways and biological functions was found analysing the differentially expressed genes in the Caco2 model in Ingenuity Pathway Analysis software following the procedure described here above (Biological function and pathway analysis with Ingenuity Pathway analysis (IPA) software). In terms of pathway modulation, the results of this analysis are as follows:

miR3126-5p modulates PI3K/AKT signalling, AHR signalling and epithelial adherens junction pathway.

miR-3141 modulates TR/RXR pathway and RXR pathway.

miR-3184-3p modulates antiproliferative role of TOB in T cell signaling.

All publications mentioned in the above specification are herein incorporated by reference. Various modifications and variations of the disclosed methods, cells, compositions and uses of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims

The invention claimed is:

1. A nutritional composition comprising miR-3126, wherein at least 50% of the miR-3126 consists of miR-3126-5p, and the remainder of the miR-3126 consists of miR-3126-3p, and wherein the nutritional composition is in a form selected from the group consisting of an infant formula, a breast milk fortifier, and an infant formula fortifier.

2. The nutritional composition according to claim 1, wherein the nutritional composition is an infant formula.

3. The nutritional composition according to claim 1, wherein the miR-3126 is present in a concentration selected from the group consisting of 0.1-10000 pmol/L, 0.1-1000 pmol/L, 1-1000 pmol/L, 10-1000 pmol/L, and 100-1000 pmol/L.

4. The nutritional composition according to claim 1, wherein the nutritional composition comprises one or more additional microRNAs selected from the group consisting of: let-7b, let-7c, miR-19b, miR-22, miR-24, miR-25, miR-29a, miR-30a, miR-92a, miR-99a, miR-100, miR-197, miR-30d, miR-181a, miR-181b, miR-205, miR-210, miR-221, miR-125b, miR-125a, miR-149, miR-193a, miR-320a, miR-200a, miR-99b, miR-130b, miR-30e, miR-375, miR-378a, miR-151a, miR-425, miR-484, miR-146b, miR-574, miR-652, miR-320c, miR-3141, let-7d, miR-196a, miR-187, miR-516a, miR-92b, and miR-3184.

5. The nutritional composition according to claim 1, wherein the nutritional composition further comprises one or more additional microRNAs selected from the group consisting of: let-7d, miR-196a, miR-187, miR-516a, miR-92b, and miR-3184.

6. The nutritional composition according to claim 1, wherein the nutritional composition further comprises miR-3141 and miR-3184.

7. The nutritional composition according to claim 1, wherein at least 95% of the miR-3126 consists of miR-3126-5p.

8. The nutritional composition according to claim 1, wherein the miR-3126 consists of miR-3126-5p.

9. The nutritional composition according to claim 1, wherein the nutritional composition comprises the miR-3126 in a concentration of 100-1000 pmol/L.

10. A method of protecting gastrointestinal health in a subject, promoting gut barrier development and function in a subject, promoting growth and development in a subject, or reducing the risk of a subject developing infectious, lymphoproliferative disorders, allergic diseases, or inflammatory diseases, comprising administering to the subject a nutritional composition comprising miR-3126, wherein at least 50% of the miR-3126 consists of miR-3126-5p, and the remainder of the miR-3126 consists of miR-3126-3p, and wherein the nutritional composition is in a form selected from the group consisting of an infant formula, a breast milk fortifier, and an infant formula fortifier.

11. The method according to claim 10, wherein the subject is an infant.

* * * * *

SEQUENCE LISTING

```
<160> NUMBER OF SEQ ID NOS: 93

<210> SEQ ID NO 1
<211> LENGTH: 74
<212> TYPE: RNA
<213> ORGANISM: Homo sapiens

<400> SEQUENCE: 1

augauuauau gagggacaga ugccagaagc acugguuaug auuugcaucu ggcauccguc     60

acacagauaa uuau                                                       74


<210> SEQ ID NO 2
<211> LENGTH: 22
<212> TYPE: RNA
<213> ORGANISM: Homo sapiens

<400> SEQUENCE: 2

ugagggacag augccagaag ca                                              22


<210> SEQ ID NO 3
<211> LENGTH: 22
<212> TYPE: RNA
<213> ORGANISM: Homo sapiens

<400> SEQUENCE: 3

caucuggcau ccgucacaca ga                                              22


<210> SEQ ID NO 4
<211> LENGTH: 22
<212> TYPE: RNA
<213> ORGANISM: Homo sapiens
<220> FEATURE:
<223> OTHER INFORMATION: let

<400> SEQUENCE: 4

ugagguagua gguugugugg uu                                              22


<210> SEQ ID NO 5
<211> LENGTH: 22
<212> TYPE: RNA
<213> ORGANISM: Homo sapiens
<220> FEATURE:
<223> OTHER INFORMATION: let

<400> SEQUENCE: 5

ugagguagua gguuguaugg uu                                              22


<210> SEQ ID NO 6
<211> LENGTH: 23
<212> TYPE: RNA
<213> ORGANISM: Homo sapiens

<400> SEQUENCE: 6

ugugcaaauc caugcaaaac uga                                             23


<210> SEQ ID NO 7
<211> LENGTH: 22
```

<212> TYPE: RNA
<213> ORGANISM: Homo sapiens

<400> SEQUENCE: 7
aagcugccag uugaagaacu gu 22

<210> SEQ ID NO 8
<211> LENGTH: 22
<212> TYPE: RNA
<213> ORGANISM: Homo sapiens

<400> SEQUENCE: 8
uggcucaguu cagcaggaac ag 22

<210> SEQ ID NO 9
<211> LENGTH: 22
<212> TYPE: RNA
<213> ORGANISM: Homo sapiens

<400> SEQUENCE: 9
cauugcacuu gucucggucu ga 22

<210> SEQ ID NO 10
<211> LENGTH: 22
<212> TYPE: RNA
<213> ORGANISM: Homo sapiens

<400> SEQUENCE: 10
uagcaccauc ugaaaucggu ua 22

<210> SEQ ID NO 11
<211> LENGTH: 22
<212> TYPE: RNA
<213> ORGANISM: Homo sapiens

<400> SEQUENCE: 11
uguaaacauc cucgacugga ag 22

<210> SEQ ID NO 12
<211> LENGTH: 22
<212> TYPE: RNA
<213> ORGANISM: Homo sapiens

<400> SEQUENCE: 12
uauugcacuu gucccggccu gu 22

<210> SEQ ID NO 13
<211> LENGTH: 22
<212> TYPE: RNA
<213> ORGANISM: Homo sapiens

<400> SEQUENCE: 13
aacccguaga uccgaucuug ug 22

<210> SEQ ID NO 14
<211> LENGTH: 22
<212> TYPE: RNA
<213> ORGANISM: Homo sapiens

<400> SEQUENCE: 14
aacccguaga uccgaacuug ug 22

<210> SEQ ID NO 15

<211> LENGTH: 22
<212> TYPE: RNA
<213> ORGANISM: Homo sapiens

<400> SEQUENCE: 15
uucaccaccu ucuccaccca gc 22

<210> SEQ ID NO 16
<211> LENGTH: 22
<212> TYPE: RNA
<213> ORGANISM: Homo sapiens

<400> SEQUENCE: 16
uguaaacauc cccgacugga ag 22

<210> SEQ ID NO 17
<211> LENGTH: 23
<212> TYPE: RNA
<213> ORGANISM: Homo sapiens

<400> SEQUENCE: 17
aacauucaac gcugucggug agu 23

<210> SEQ ID NO 18
<211> LENGTH: 23
<212> TYPE: RNA
<213> ORGANISM: Homo sapiens

<400> SEQUENCE: 18
aacauucauu gcugucggug ggu 23

<210> SEQ ID NO 19
<211> LENGTH: 22
<212> TYPE: RNA
<213> ORGANISM: Homo sapiens

<400> SEQUENCE: 19
uccuucauuc caccggaguc ug 22

<210> SEQ ID NO 20
<211> LENGTH: 22
<212> TYPE: RNA
<213> ORGANISM: Homo sapiens

<400> SEQUENCE: 20
cugugcgugu gacagcggcu ga 22

<210> SEQ ID NO 21
<211> LENGTH: 23
<212> TYPE: RNA
<213> ORGANISM: Homo sapiens

<400> SEQUENCE: 21
agcuacauug ucugcugggu uuc 23

<210> SEQ ID NO 22
<211> LENGTH: 22
<212> TYPE: RNA
<213> ORGANISM: Homo sapiens

<400> SEQUENCE: 22
ucccugagac ccuaacuugu ga 22

<210> SEQ ID NO 23
<211> LENGTH: 24
<212> TYPE: RNA
<213> ORGANISM: Homo sapiens

<400> SEQUENCE: 23
ucccugagac ccuuuaaccu guga 24

<210> SEQ ID NO 24
<211> LENGTH: 21
<212> TYPE: RNA
<213> ORGANISM: Homo sapiens

<400> SEQUENCE: 24
agggagggac gggggcugug c 21

<210> SEQ ID NO 25
<211> LENGTH: 22
<212> TYPE: RNA
<213> ORGANISM: Homo sapiens

<400> SEQUENCE: 25
ugggucuuug cgggcgagau ga 22

<210> SEQ ID NO 26
<211> LENGTH: 22
<212> TYPE: RNA
<213> ORGANISM: Homo sapiens

<400> SEQUENCE: 26
aacuggccua caaagUccca gu 22

<210> SEQ ID NO 27
<211> LENGTH: 22
<212> TYPE: RNA
<213> ORGANISM: Homo sapiens

<400> SEQUENCE: 27
aaaagcuggg uugagagggc ga 22

<210> SEQ ID NO 28
<211> LENGTH: 22
<212> TYPE: RNA
<213> ORGANISM: Homo sapiens

<400> SEQUENCE: 28
uaacacuguc ugguaacgau gu 22

<210> SEQ ID NO 29
<211> LENGTH: 22
<212> TYPE: RNA
<213> ORGANISM: Homo sapiens

<400> SEQUENCE: 29
cacccguaga accgaccuug cg 22

<210> SEQ ID NO 30
<211> LENGTH: 22
<212> TYPE: RNA
<213> ORGANISM: Homo sapiens

<400> SEQUENCE: 30
cagugcaaug augaaagggc au 22

<210> SEQ ID NO 31
<211> LENGTH: 22
<212> TYPE: RNA
<213> ORGANISM: Homo sapiens

<400> SEQUENCE: 31
uguaaacauc cuugacugga ag 22

<210> SEQ ID NO 32
<211> LENGTH: 22
<212> TYPE: RNA
<213> ORGANISM: Homo sapiens

<400> SEQUENCE: 32
uuuguucguu cggcucgcgu ga 22

<210> SEQ ID NO 33
<211> LENGTH: 22
<212> TYPE: RNA
<213> ORGANISM: Homo sapiens

<400> SEQUENCE: 33
acuggacuug gagucagaag gc 22

<210> SEQ ID NO 34
<211> LENGTH: 21
<212> TYPE: RNA
<213> ORGANISM: Homo sapiens

<400> SEQUENCE: 34
cuagacugaa gcuccuugag g 21

<210> SEQ ID NO 35
<211> LENGTH: 23
<212> TYPE: RNA
<213> ORGANISM: Homo sapiens

<400> SEQUENCE: 35
aaugacacga ucacucccgu uga 23

<210> SEQ ID NO 36
<211> LENGTH: 22
<212> TYPE: RNA
<213> ORGANISM: Homo sapiens

<400> SEQUENCE: 36
ucaggcucag uccccucccg au 22

<210> SEQ ID NO 37
<211> LENGTH: 22
<212> TYPE: RNA
<213> ORGANISM: Homo sapiens

<400> SEQUENCE: 37
ugagaacuga auuccauagg cu 22

<210> SEQ ID NO 38
<211> LENGTH: 23
<212> TYPE: RNA
<213> ORGANISM: Homo sapiens

<400> SEQUENCE: 38
ugagugugug ugugugagug ugu 23

<210> SEQ ID NO 39
<211> LENGTH: 21
<212> TYPE: RNA
<213> ORGANISM: Homo sapiens

<400> SEQUENCE: 39
aauggcgcca cuaggguugu g 21

<210> SEQ ID NO 40
<211> LENGTH: 20
<212> TYPE: RNA
<213> ORGANISM: Homo sapiens

<400> SEQUENCE: 40
aaaagcuggg uugagagggu 20

<210> SEQ ID NO 41
<211> LENGTH: 19
<212> TYPE: RNA
<213> ORGANISM: Homo sapiens

<400> SEQUENCE: 41
gagggcgggu ggaggagga 19

<210> SEQ ID NO 42
<211> LENGTH: 17
<212> TYPE: RNA
<213> ORGANISM: Homo sapiens

<400> SEQUENCE: 42
gaggcugagc ugaggag 17

<210> SEQ ID NO 43
<211> LENGTH: 22
<212> TYPE: RNA
<213> ORGANISM: Homo sapiens

<400> SEQUENCE: 43
cuauacgacc ugcugccuuu cu 22

<210> SEQ ID NO 44
<211> LENGTH: 22
<212> TYPE: RNA
<213> ORGANISM: Homo sapiens

<400> SEQUENCE: 44
uagguaguuu cauguuguug gg 22

<210> SEQ ID NO 45
<211> LENGTH: 22
<212> TYPE: RNA
<213> ORGANISM: Homo sapiens

<400> SEQUENCE: 45
ggcuacaaca caggacccgg gc 22

<210> SEQ ID NO 46
<211> LENGTH: 23
<212> TYPE: RNA
<213> ORGANISM: Homo sapiens

<400> SEQUENCE: 46
uucucgagga aagaagcacu uuc 23

<210> SEQ ID NO 47
<211> LENGTH: 22
<212> TYPE: RNA
<213> ORGANISM: Homo sapiens

<400> SEQUENCE: 47
agggacggga cgcggugcag ug 22

<210> SEQ ID NO 48
<211> LENGTH: 23
<212> TYPE: RNA
<213> ORGANISM: Homo sapiens

<400> SEQUENCE: 48
aaagucucgc ucucugcccc uca 23

<210> SEQ ID NO 49
<211> LENGTH: 22
<212> TYPE: RNA
<213> ORGANISM: Bos taurus
<220> FEATURE:
<223> OTHER INFORMATION: let

<400> SEQUENCE: 49
ugagguagua gguugugugg uu 22

<210> SEQ ID NO 50
<211> LENGTH: 22
<212> TYPE: RNA
<213> ORGANISM: Bos taurus
<220> FEATURE:
<223> OTHER INFORMATION: let

<400> SEQUENCE: 50
ugagguagua gguuguaugg uu 22

<210> SEQ ID NO 51
<211> LENGTH: 23
<212> TYPE: RNA
<213> ORGANISM: Bos taurus

<400> SEQUENCE: 51
ugugcaaauc caugcaaaac uga 23

<210> SEQ ID NO 52
<211> LENGTH: 21
<212> TYPE: RNA
<213> ORGANISM: Bos taurus

<400> SEQUENCE: 52
aagcugccag uugaagaacu g 21

<210> SEQ ID NO 53
<211> LENGTH: 22
<212> TYPE: RNA
<213> ORGANISM: Bos taurus

<400> SEQUENCE: 53
uggcucaguu cagcaggaac ag 22

<210> SEQ ID NO 54
<211> LENGTH: 22

<212> TYPE: RNA
<213> ORGANISM: Bos taurus

<400> SEQUENCE: 54
cauugcacuu gucucggucu ga 22

<210> SEQ ID NO 55
<211> LENGTH: 23
<212> TYPE: RNA
<213> ORGANISM: Bos taurus

<400> SEQUENCE: 55
cuagcaccau cugaaaucgg uua 23

<210> SEQ ID NO 56
<211> LENGTH: 24
<212> TYPE: RNA
<213> ORGANISM: Bos taurus

<400> SEQUENCE: 56
uguaaacauc cucgacugga agcu 24

<210> SEQ ID NO 57
<211> LENGTH: 22
<212> TYPE: RNA
<213> ORGANISM: Bos taurus

<400> SEQUENCE: 57
uauugcacuu gucccggccu gu 22

<210> SEQ ID NO 58
<211> LENGTH: 21
<212> TYPE: RNA
<213> ORGANISM: Bos taurus

<400> SEQUENCE: 58
aacccguaga uccgaucuug u 21

<210> SEQ ID NO 59
<211> LENGTH: 22
<212> TYPE: RNA
<213> ORGANISM: Bos taurus

<400> SEQUENCE: 59
aacccguaga uccgaacuug ug 22

<210> SEQ ID NO 60
<211> LENGTH: 22
<212> TYPE: RNA
<213> ORGANISM: Bos taurus

<400> SEQUENCE: 60
uucaccaccu ucuccaccca gc 22

<210> SEQ ID NO 61
<211> LENGTH: 24
<212> TYPE: RNA
<213> ORGANISM: Bos taurus

<400> SEQUENCE: 61
uguaaacauc cccgacugga agcu 24

<210> SEQ ID NO 62

<211> LENGTH: 24
<212> TYPE: RNA
<213> ORGANISM: Bos taurus

<400> SEQUENCE: 62
aacauucaac gcugucggug aguu 24

<210> SEQ ID NO 63
<211> LENGTH: 24
<212> TYPE: RNA
<213> ORGANISM: Bos taurus

<400> SEQUENCE: 63
aacauucauu gcugucggug gguu 24

<210> SEQ ID NO 64
<211> LENGTH: 22
<212> TYPE: RNA
<213> ORGANISM: Bos taurus

<400> SEQUENCE: 64
uccuucauuc caccggaguc ug 22

<210> SEQ ID NO 65
<211> LENGTH: 23
<212> TYPE: RNA
<213> ORGANISM: Bos taurus

<400> SEQUENCE: 65
acugugcgug ugacagcggc uga 23

<210> SEQ ID NO 66
<211> LENGTH: 22
<212> TYPE: RNA
<213> ORGANISM: Bos taurus

<400> SEQUENCE: 66
agcuacauug ucugcugggu uu 22

<210> SEQ ID NO 67
<211> LENGTH: 22
<212> TYPE: RNA
<213> ORGANISM: Bos taurus

<400> SEQUENCE: 67
ucccugagac ccuaacuugu ga 22

<210> SEQ ID NO 68
<211> LENGTH: 23
<212> TYPE: RNA
<213> ORGANISM: Bos taurus

<400> SEQUENCE: 68
ucccugagac ccuuuaaccu gug 23

<210> SEQ ID NO 69
<211> LENGTH: 22
<212> TYPE: RNA
<213> ORGANISM: Bos taurus

<400> SEQUENCE: 69
gagggaggga cgggggcugu gc 22

<210> SEQ ID NO 70
<211> LENGTH: 22
<212> TYPE: RNA
<213> ORGANISM: Bos taurus

<400> SEQUENCE: 70
ugggucuuug cgggcgagau ga 22

<210> SEQ ID NO 71
<211> LENGTH: 22
<212> TYPE: RNA
<213> ORGANISM: Bos taurus

<400> SEQUENCE: 71
aacuggccua caaaguccca gu 22

<210> SEQ ID NO 72
<211> LENGTH: 22
<212> TYPE: RNA
<213> ORGANISM: Bos taurus

<400> SEQUENCE: 72
aaaagcuggg uugagagggc ga 22

<210> SEQ ID NO 73
<211> LENGTH: 23
<212> TYPE: RNA
<213> ORGANISM: Bos taurus

<400> SEQUENCE: 73
uaacacuguc ugguaacgau guu 23

<210> SEQ ID NO 74
<211> LENGTH: 22
<212> TYPE: RNA
<213> ORGANISM: Bos taurus

<400> SEQUENCE: 74
cacccguaga accgaccuug cg 22

<210> SEQ ID NO 75
<211> LENGTH: 22
<212> TYPE: RNA
<213> ORGANISM: Bos taurus

<400> SEQUENCE: 75
cagugcaaug augaaagggc au 22

<210> SEQ ID NO 76
<211> LENGTH: 24
<212> TYPE: RNA
<213> ORGANISM: Bos taurus

<400> SEQUENCE: 76
uguaaacauc cuugacugga agcu 24

<210> SEQ ID NO 77
<211> LENGTH: 23
<212> TYPE: RNA
<213> ORGANISM: Bos taurus

<400> SEQUENCE: 77
uuuuguucgu ucggcucgcg uga 23

<210> SEQ ID NO 78
<211> LENGTH: 22
<212> TYPE: RNA
<213> ORGANISM: Bos taurus

<400> SEQUENCE: 78
acuggacuug gagucagaag gc 22

<210> SEQ ID NO 79
<211> LENGTH: 21
<212> TYPE: RNA
<213> ORGANISM: Bos taurus

<400> SEQUENCE: 79
cuagacugaa gcuccuugag g 21

<210> SEQ ID NO 80
<211> LENGTH: 22
<212> TYPE: RNA
<213> ORGANISM: Bos taurus

<400> SEQUENCE: 80
augacacgau cacucccguu ga 22

<210> SEQ ID NO 81
<211> LENGTH: 22
<212> TYPE: RNA
<213> ORGANISM: Bos taurus

<400> SEQUENCE: 81
ucaggcucag uccccucccg au 22

<210> SEQ ID NO 82
<211> LENGTH: 24
<212> TYPE: RNA
<213> ORGANISM: Bos taurus

<400> SEQUENCE: 82
ugagaacuga auuccauagg cugu 24

<210> SEQ ID NO 83
<211> LENGTH: 24
<212> TYPE: RNA
<213> ORGANISM: Bos taurus

<400> SEQUENCE: 83
ugagugugug ugugugagug ugug 24

<210> SEQ ID NO 84
<211> LENGTH: 21
<212> TYPE: RNA
<213> ORGANISM: Bos taurus

<400> SEQUENCE: 84
aauggcgcca cuaggguugu g 21

<210> SEQ ID NO 85
<211> LENGTH: 20
<212> TYPE: RNA
<213> ORGANISM: Bos taurus

<400> SEQUENCE: 85
agcuggguug agaggguggu 20

<210> SEQ ID NO 86
<211> LENGTH: 18
<212> TYPE: RNA
<213> ORGANISM: Bos taurus

<400> SEQUENCE: 86
gagggcgggu ggaggagg 18

<210> SEQ ID NO 87
<211> LENGTH: 22
<212> TYPE: RNA
<213> ORGANISM: Bos taurus
<220> FEATURE:
<223> OTHER INFORMATION: let

<400> SEQUENCE: 87
agagguagua gguugcauag uu 22

<210> SEQ ID NO 88
<211> LENGTH: 22
<212> TYPE: RNA
<213> ORGANISM: Bos taurus

<400> SEQUENCE: 88
uagguaguuu cauguuguug gg 22

<210> SEQ ID NO 89
<211> LENGTH: 22
<212> TYPE: RNA
<213> ORGANISM: Bos taurus

<400> SEQUENCE: 89
ucgugucuug uguugcagcc gg 22

<210> SEQ ID NO 90
<211> LENGTH: 22
<212> TYPE: RNA
<213> ORGANISM: Bos taurus

<400> SEQUENCE: 90
uauugcacuc gucccggccu cc 22

<210> SEQ ID NO 91
<211> LENGTH: 22
<212> TYPE: RNA
<213> ORGANISM: Homo sapiens

<400> SEQUENCE: 91
uggcaguguc uuagcugguu gu 22

<210> SEQ ID NO 92
<211> LENGTH: 22
<212> TYPE: RNA
<213> ORGANISM: Homo sapiens

<400> SEQUENCE: 92
ugagaacuga auuccauggg uu 22

<210> SEQ ID NO 93
<211> LENGTH: 22

-continued

```
<212> TYPE: RNA
<213> ORGANISM: Homo sapiens

<400> SEQUENCE: 93

acucggcgug gcgucggucg ug                                            22
```